United States Patent
Kelly et al.

(10) Patent No.: US 10,929,480 B2
(45) Date of Patent: Feb. 23, 2021

(54) BOLUS DISPLAY AND DOCUMENTATION

(71) Applicant: CERNER INNOVATION, INC., Kansas City, KS (US)

(72) Inventors: Lisa Kelly, Overland Park, KS (US); Judith A. Zakutny, Olathe, KS (US); Bryan Muehlmeier, Overland Park, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 920 days.

(21) Appl. No.: 14/587,493

(22) Filed: Dec. 31, 2014

(65) Prior Publication Data

US 2016/0125164 A1 May 5, 2016

Related U.S. Application Data

(60) Provisional application No. 62/074,463, filed on Nov. 3, 2014.

(51) Int. Cl.
| | |
|---|---|
| *G16H 40/63* | (2018.01) |
| *G16H 40/20* | (2018.01) |
| *G06F 19/00* | (2018.01) |
| *A61M 5/14* | (2006.01) |
| *G06F 16/951* | (2019.01) |
| *G16H 50/30* | (2018.01) |

(52) U.S. Cl.
CPC .......... *G06F 16/951* (2019.01); *G06F 19/328* (2013.01); *G06F 19/3418* (2013.01); *G06F 19/3462* (2013.01); *G06F 19/3468* (2013.01); *G16H 40/20* (2018.01); *G16H 40/63* (2018.01); *G16H 50/30* (2018.01); *A61M 5/14* (2013.01)

(58) Field of Classification Search
None
See application file for complete search history.

(56) References Cited

U.S. PATENT DOCUMENTS

| | | | |
|---|---|---|---|
| 6,069,877 A | 5/2000 | Yang | |
| 8,400,295 B1 | 3/2013 | Khaira | |
| 2003/0078811 A1 | 4/2003 | Cole et al. | |
| 2003/0145854 A1 | 8/2003 | Hickle | |
| 2004/0172301 A1* | 9/2004 | Mihai | A61B 5/0002 |
| | | | 705/2 |
| 2006/0064020 A1 | 3/2006 | Burnes et al. | |

(Continued)

OTHER PUBLICATIONS

First Action Interview Preinterview Communication dated Jun. 26, 2017 in U.S. Appl. No. 14/587,507, 5 pages.

(Continued)

*Primary Examiner* — Devin C Hein
(74) *Attorney, Agent, or Firm* — Shook Hardy & Bacon LLP

(57) ABSTRACT

Methods, computer systems and computer readable media for receiving data and information from medical devices in a healthcare setting are provided. In embodiments, an indication that a bolus is being administered to a patient in association with the infusion is received. Accordingly a graphical indication the bolus is running is provided, the indication causing a volume remaining and the rate of the infusion to be temporarily masked until the bolus is completed. In embodiments, a graphical indication is provided that indicates an infusion is being administered.

19 Claims, 30 Drawing Sheets

(56) References Cited

U.S. PATENT DOCUMENTS

| | | |
|---|---|---|
| 2006/0132292 A1* | 6/2006 | Blomquist ............ A61M 5/142 |
| | | 340/309.16 |
| 2007/0118410 A1 | 5/2007 | Nadai |
| 2008/0033749 A1 | 2/2008 | Blomquist |
| 2009/0048865 A1 | 2/2009 | Breazeale, Jr. |
| 2009/0112630 A1 | 4/2009 | Collins, Jr. et al. |
| 2011/0035690 A1* | 2/2011 | Durrell ................ G06Q 10/06 |
| | | 715/764 |
| 2011/0119612 A1* | 5/2011 | Gannon ................ G06F 3/0481 |
| | | 715/771 |
| 2013/0013338 A1 | 1/2013 | DeBelser et al. |
| 2013/0117384 A1 | 5/2013 | Martch |
| 2013/0316649 A1 | 11/2013 | Newham |
| 2013/0321145 A1 | 12/2013 | Ranieri et al. |

OTHER PUBLICATIONS

First Action Interview Preinterview Communication dated Aug. 30, 2017 in U.S. Appl. No. 14/587,501, 4 pages.
First Action Interview Preinterview Communication dated Sep. 1, 2017 in U.S. Appl. No. 14/587,516, 4 pages.
First Action Interview Office Action dated Oct. 27, 2017 in U.S. Appl. No. 14/587,507, 4 pages.
First Action Interview Office Action dated Dec. 4, 2017 in U.S. Appl. No. 14/587,501, 3 pages.
First Action Interview Office Action dated Dec. 5, 2017 in U.S. Appl. No. 14/587,516, 3 pages.
Final Office Action dated Jun. 15, 2018 in U.S. Appl. No. 15/587,507, 18 pages.
Final Office Action dated Aug. 8, 2018 in U.S. Appl. No. 14/587,501, 28 pages.
Final Office Action dated Aug. 10, 2018 in U.S. Appl. No. 14/587,516, 16 pages.
Final Office Action received for U.S. Appl. No. 14/587,507, dated May 29, 2019, 15 pages.
Non Final Office Action received for U.S. Appl. No. 14/587,507, dated Nov. 18, 2019, 20 pages.
Final Office Action received for U.S. Appl. No. 14/587,501, dated Jun. 9, 2020, 33 pages.
Final Office Action received for U.S. Appl. No. 14/587,507, dated Jun. 2, 2020, 21 pages.

* cited by examiner

FIG. 3

Infusion Status ✕

Insulin Regular IV ordered at 5 units/hr
Current Rate: 8 mL/hr
Calculated Dose Rate: 5 units/hr <30 min

Lasix IV ordered at 1 mg/mL
Current Rate: 1 mL/hr
Calculated Dose Rate: -- — 410

Bolus — 420

Sodium Chloride 0.45% + 20 mEq KCL IV ordered at 50 mL/hr
Current Rate: 50 mL/hr
Calculated Dose Rate: 50 units/hr <2 hr

Terbutaline IV ordered at 3 mcg/kg/min
Current Rate: 10 mL/hr
Calculated Dose Rate: 3 mcg/kg/min <2 hr

Propofol IV ordered at 62.5 mcg/kg/min
Current Rate: 1 mL/hr
Calculated Dose Rate: 62.5 mcg/kg/min <4 hr

| Pharmacy Infusion Management | | | | | | |
|---|---|---|---|---|---|---|
| Pharmacy Infusion Status ✕ | | | | | Reset Perspective ☐ ☐ 🔄 no patient | |
| Displayed location(s): All | | | | | | 🕐 0 minute ago |
| Patient | Location | Medication | Current Infusion | Distribution Status | Time Remaining | Priority |
| Mike Gonzoles<br>56 \| Male \| FIN: 17784 | 2 East/2145 | Sodium Chloride 0.9% 1,000 mL + Potassium Chloride 35 mEQ IV ordered at 125 mL/hr | <5 hr<br>100 mL/hr | 1  Delivered | 0 min | ☑ |
| Kimberly Brown<br>62 \| Female \| FIN: 0009331 | 2 West/2147 | amiodarone (1.5 mg/mL) IV ordered at 5 mcg/kg/min | <18 min<br>12 mL/hr | | 18 min | ⊘ |
| Max Walker<br>64 \| Male \| FIN: 000009421 | 2 West/2220 | Nitroprusside (200 mcg/mL) IV Ordered at 3 mcg/kg/min | <34 min<br>54 mL/hr | | 34 min | ⊘ |
| Jackson McMann<br>66 \| Male \| FIN: 1778421 | 2 West/2221 | propofol (10 mg/mL) IV ordered at 2 mg/kg/hr | <57 min<br>9 mL/hr | | 57 min | ⊘ |
| Victor Carville<br>64 \| Male \| FIN: 3301872 | CCU/02 | Lasix IV ordered at 1 mg/mL | <2 hr<br>10 mL/hr | 1  Delivered | Bolus | ® |
| Summer Lester<br>90 \| Female \| FIN: 17786 | 2 North/2145 | Sodium Chloride 0.9% 1,000 mL + Potassium Chloride 25 mEq IV Ordered at 18 mL/hr | <3 hr<br>18 mL/hr | | 3 hrs | |
| Sherry Delong<br>37 \| Female \| FIN: 17784 | CCU/001 | DOPamine(3.2 mg/mL) IV Ordered at 20 mcg/kg/min | <9 hr<br>22.5 mL/hr | 1  Ready to deliver | 9 hrs | |
| Summer Lester<br>90\| Male \| FIN: 17786 | 2 North/2145 | Nitroglycerin (0.2 mg/mL) IV Ordered at 1.2 mg/hr | <12 hr<br>20 mL/hr | 1  UNKNOWN | | ◇ |
| Smith George<br>10 \| Male \| FIN: 050820934832 | PICU/Pavillion/7S-701 | propofol 10 mg/mL Ordered at 3 mg/kg/hr | <39 hr<br>7.1 mL/hr | | 14 hrs 43 min | |
| Megan Moore<br>86 \| Female \| FIN: 17786 | CCU/03 | DOPamine (3.2 mg/mL) IV Ordered at 10 mcg/kg/min | <15 hr<br>15 mL/hr | 1  Delivered | 30 hrs 33 min | |
| Alexander Martin<br>50 \| Male \| FIN: 90876432 | CCU/05 | DOPamine (3.2 mg/mL) IV Ordered at 10 mcg/kg/min | Stopped<br>15 mL/hr | 1  Ready to prepare | Stopped<br>15 hrs | |

500 ← (table reference)
510 ← (Victor Carville row indicator)

| Items | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 |
|---|---|---|---|---|---|---|---|---|---|---|---|---|---|---|---|
| ▼ Vital Signs | | | | | | | | | | | | | | | |
| T (core) degC | 37.2 | | | 37.2 | | 37.2 | 37.2 | 37.2 | 37.2 | 37.2 | 39 | 37.5 | 37.4 | 37.2 | 39 |
| HR bpm | 88 | | | 88 | | 88 | 92 | 97 | 95 | 86 | 90 | 87 | 87 | 87 | 88 |
| RR bpm | 20 | | | 20 | | 20 | 16 | 30 | 21 | 29 | 21 | 19 | 20 | 19 | 28 |
| SBP/DBP Cuff | 102/59 | | | 102/59 | | 102/59 | 101/56 | 101/56 | 99.8/60 | 116/54 | 102/55 | 99.6/58 | 100/58 | 99.2/57 | 110/68 |
| MAP Cuff | 73 | | | 73 | | 73 | 71 | 71 | 73 | 75 | 71 | 72 | 72 | 71 | 82 |
| O2 Sat % | 87 | | | 87 | | 87 | 86 | 88 | 86 | 92 | 87 | 86 | 86 | 86 | 46 |
| Cardiac Rhythm | | | | | | | | | | | | | | | bradyca... |
| ▼ Hemodynamics | | | | | | | | | | | | | | | |
| CVP CVP | | | | | | 3 | 4 | 2 | 4 | 2 | 2 | 2 | 4 | 2 | 2 |
| PAS PAS | | | | | | 27 | 20 | 20 | 20 | 20 | 20 | 20 | 20 | 20 | 20 |
| PAD PADP | | | | | | 5 | 5 | 5 | 5 | 5 | 5 | 5 | 5 | 5 | 5 |
| ▼ Intake | | | | | | | | | | | | | | | |
| Intake Total | 125 | | | | | | | | | | | | | | |
| ☐ Insulin (1 unit/mL) IV ordered at 2... units/hr | 2 | | | 2 | | 2 | 3 | 3 | 2 | 2 | 2 | 2 | 4 | 2 | |
| Rate mL/hr | 4 | | | 4 | | 4 | 6 | 6 | 4 | 4 | 4 | | | 4 | |
| Vol Infused mL | 4 | | | 4 | | 4 | 6 | | | | | | | 4 | |
| ☐ Lasix (1 mg/mL) IV ordered at 0... mg/hr | | | 10 | 4 | Bolus: 20 mL Infusion: 4 mL | | | | | | | | | | |
| Rate mg/hr | | | 10 | 4 | | | | | | | | | | | |
| Bolus mg | | 10 | | | | | | | | | | | | | |
| Vol Infused mL | | | | | | | | | | | | | | | |
| ☐ Propofol (10mg/mL) IV ordered at 8... mcg/kg/min | 50.6 | | | 50.6 | | 50.6 | 50.6 | | 50.6 | | 62.5 | | | 62.5 | |
| Rate mL/hr | 23.5 | | | 23.5 | | 23.5 | 23.5 | | 23.5 | | 29 | | | 29 | |
| Vol Infused mL | 23.5 | | | 23.5 | | 23.5 | 23.5 | | 23.5 | | 29 | | | 29 | |
| ☐ Terbutaline (3mcg/kg/min) IV order... mcg/kg/min | 2 | | | 2 | | 2 | 2 | | 2 | | 2 | | | 2 | |
| Rate mL/hr | 15 | | | 15 | | 15 | 15 | | 15 | | 15 | | | 15 | |
| Vol Infused mL | 15 | | | 15 | | 15 | 15 | | 15 | | 15 | | | 15 | |
| ☐ Sodium Chloride 0.45% ordered at 1 mL/hr | 50 | | | 50 | | 50 | | 50 | | | 50 | | | 50 | |
| Bolus mL | | | | | | | 250 | | | | | | | | |
| Vol Infused mL | 50 | | | 50 | | 50 | | 50 | | | 50 | | | 50 | |
| ▲ Medication Infusions | | | | | | | | | | | | | | | |
| Ceftriaxone 1g IV Q12hr mL | | | | 100 | | | | | | | 100 | | | | |
| Metoclopramide 10 mg IV QID mL | | | | | | | | | | | | | | | |
| ▲ Other Intake | | | | | | | | | | | | | | | |
| Oral Intake mL | | | | | | 100 | | | | | | | | | |
| ▶ Output | | | | | | | | | | | | | | | |
| Output Total | 105 | | | | | | | | | | | | | | |
| Urine Voided mL | | | | | 90 | | | | | | | | | | |
| Urine Catheter mL | | | | | 15 | | | | | | | | | | |
| ☐ Chest Tubes | | | | | | | | | | | | | | | |
| Right anterior 20 French | | | | | | | | | | | | | | | |
| Output mL | | | | | | | | | | | | | | | |
| Net | -85 | | | | | | | | | | | | | | |

FIG. 9

| Items | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 |
|---|---|---|---|---|---|---|---|---|---|---|---|---|---|---|---|
| ▼ Vital Signs | | | | | | | | | | | | | | | |
| T (core) degC | 37.2 | | | 37.2 | | 37.2 | 37.2 | 37.2 | 37.2 | 37.2 | 39 | 37.5 | 37.4 | 37.2 | 39 |
| HR bpm | 88 | | | 88 | | 88 | 92 | 97 | 95 | 86 | 90 | 87 | 87 | 87 | 88 |
| RR bpm | 20 | | | 20 | | 20 | 16 | 30 | 21 | 29 | 21 | 19 | 20 | 19 | 28 |
| SBP/DBP Cuff | 102/59 | | | 102/59 | | 102/59 | 101/56 | 101/56 | 99.8/60 | 116/54 | 102/55 | 99.6/58 | 100/58 | 99.2/57 | 110/68 |
| MAP Cuff | 73 | | | 73 | | 73 | 71 | 71 | 73 | 75 | 71 | 72 | 72 | 71 | 82 |
| O2 Sat % | 87 | | | 87 | | 87 | 86 | 88 | 86 | 92 | 87 | 86 | 86 | 86 | 46 |
| Cardiac Rhythm | | | | | | | | | | | | | | | bradyca... |
| ▼ Hemodynamics | | | | | | | | | | | | | | | |
| CVP CVP | | | | | | 3 | 4 | 2 | 4 | 4 | 2 | 2 | 4 | 4 | 2 |
| PAS PAS | | | | | | 27 | 20 | 20 | 5 | 20 | 20 | 20 | 20 | 20 | 20 |
| PAD PADP | | | | | | 5 | 5 | 5 | 5 | 5 | 5 | 5 | 5 | 5 | 5 |
| ▼ Intake | | | | | | | | | | | | | | | |
| Intake Total | 125 | | | | | | | | | | | | | | |
| ☐ Insulin (1 unit/mL) IV ordered at 2... units/hr | 2 | | | 2 | | 2 | 3 | 3 | 2 | 2 | 2 | 2 | | 2 | |
| Rate mL/hr | 4 | | | 4 | | 4 | 6 | 6 | 4 | 4 | 4 | | | 4 | |
| Vol Infused mL | 4 | | | 4 | | 4 | 6 | | | | 4 | | | 4 | |
| ☐ Lasix (1 mg/mL) IV ordered at 0 ... mg/hr | | 10 | 10 | | | | | | | | | | | | |
| Rate mg/hr | | | | | | | | | | | | | | | |
| Bolus mg | | 10 | 10 | | | | | | | | | | | | |
| Vol Infused mL | | | | 24 | | | | | | | | | | | |
| ☐ Propofol (10mg/mL) IV ordered at 8... mcg/kg/min | 50.6 | | | 50.6 | | 50.6 | 50.6 | | 50.6 | | 62.5 | | | 62.5 | |
| Rate mL/hr | 23.5 | | | 23.5 | | 23.5 | 23.5 | | 23.5 | | 29 | | | 29 | |
| Vol Infused mL | 23.5 | | | 23.5 | | 23.5 | 23.5 | | 23.5 | | 29 | | | 29 | |
| ☐ Terbutaline (3mcg/kg/min) IV order... mcg/kg/min | 2 | | | 2 | | 2 | 2 | | 2 | | 2 | | | 2 | |
| Rate mL/hr | 15 | | | 15 | | 15 | 15 | | 15 | | 15 | | | 15 | |
| Vol Infused mL | 15 | | | 15 | | 15 | 15 | | 15 | | 15 | | | 15 | |
| ☐ Sodium Chloride 0.45% ordered at 1 mL/hr | 50 | | | 50 | | 50 | | 50 | | | 50 | | | 50 | |
| Bolus mL | | | | | | | 250 | | | | | | | | |
| Vol Infused mL | 50 | | | 50 | | 50 | | 50 | | | 50 | | | 50 | |
| ▲ Medication Infusions | | | | | | | | | | | | | | | |
| Ceftriaxone 1g IV Q12hr mL | | | | 100 | | | | | | | 100 | | | | |
| Metoclopramide 10 mg IV QID mL | | | | | | | | | | | | | | | |
| ▲ Other Intake | | | | | | | | | | | | | | | |
| Oral Intake mL | | | | | | | | | | | | | | | |
| ▶ Output | | | | | | | | | | | | | | | |
| Output Total | 105 | | | | | | | | | | | | | | |
| Urine Voided mL | | | | | | 90 | | | | | | | | | |
| Urine Catheter mL | | | | | | 15 | | | | | | | | | |
| ☐ Chest Tubes | | | | | | | | | | | | | | | |
| Right anterior 20 French Output mL | | | | | | | | | | | | | | | |
| Net | -85 | | | | | | | | | | | | | | |

| Items | | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 |
|---|---|---|---|---|---|---|---|---|---|---|---|---|---|---|---|---|
| ▼ Vital Signs | | | | | | | | | | | | | | | | |
| | T (core) degC | 37.2 | | | 37.2 | | 37.2 | 37.2 | 37.2 | 37.2 | 37.2 | 39 | 37.5 | 37.4 | 37.2 | 39 |
| | HR bpm | 88 | | | 88 | | 88 | 92 | 97 | 95 | 86 | 90 | 87 | 87 | 87 | 88 |
| | RR bpm | 20 | | | 20 | | 20 | 16 | 30 | 21 | 29 | 21 | 19 | 20 | 19 | 28 |
| | SBP/DBP Cuff | 102/59 | | | 102/59 | | 102/59 | 101/56 | 101/56 | 99.8/60 | 116/54 | 102/55 | 99.6/58 | 100/58 | 99.2/57 | 110/68 |
| | MAP Cuff | 73 | | | 73 | | 73 | 71 | 71 | 73 | 75 | 71 | 72 | 72 | 71 | 82 |
| | O2 Sat % | 87 | | | 87 | | 87 | 86 | 88 | 86 | 92 | 87 | 86 | 86 | 86 | 46 |
| | Cardiac Rhythm | | | | | | | | | | | | | | | bradyca... |
| ▼ Hemodynamics | | | | | | | | | | | | | | | | |
| | CVP CVP | | | | | | 3 | 4 | 2 | 4 | 4 | 2 | 2 | 4 | 2 | |
| | PAS PAS | | | | | | 27 | 20 | 20 | 20 | 20 | 20 | 20 | 20 | 20 | |
| | PAD PADP | | | | | | 5 | 5 | 5 | 5 | 5 | 5 | 5 | 5 | 5 | |
| ▼ Intake | | | | | | | | | | | | | | | | |
| Intake Total | | 125 | | | | | | | | | | | | | | |
| ☐ Insulin (1 unit/mL) | IV ordered at 2... units/hr | 2 | | | 2 | | 2 | 3 | 3 | 2 | 2 | 2 | | | 2 | |
| | Rate mL/hr | 4 | | | 4 | | 4 | 6 | 6 | 4 | 4 | 4 | | | 4 | |
| | Vol Infused mL | 4 | | | 4 | | 4 | 6 | | | | | | | 4 | |
| ☐ Lasix (1 mg/mL) | IV ordered at 0... mg/hr | | | | | | | | | | | | | | | |
| | Rate mg/hr | | | | | | | | | | | | | | | |
| | Bolus mg | | 10 | 10 | | | | | | | | | | | | |
| | Vol Infused mL | | 10 | 10 | 24 | | 4 | | | | | | | | | |
| ☐ Propofol (10mg/mL) | IV ordered at 8... mcg/kg/min | 50.6 | | | 50.6 | | 50.6 | 50.6 | | 50.6 | | 62.5 | | | 62.5 | |
| | Rate mL/hr | 23.5 | | | 23.5 | | 23.5 | 23.5 | | 23.5 | | 29 | | | 29 | |
| | Vol Infused mL | 23.5 | | | 23.5 | | 23.5 | 23.5 | | 23.5 | | 29 | | | 29 | |
| ☐ Terbutaline (3mcg/kg/min) | IV order... mcg/kg/min | 2 | | | 2 | | 2 | 2 | | 2 | | 2 | | | 2 | |
| | Rate mL/hr | 15 | | | 15 | | 15 | 15 | | 15 | | 15 | | | 15 | |
| | Vol Infused mL | 15 | | | 15 | | 15 | 15 | | 15 | | 15 | | | 15 | |
| ☐ Sodium Chloride 0.45% | ordered at 1 mL/hr | 50 | | | 50 | | 50 | | 50 | | | 50 | | | 50 | |
| | Bolus mL | | | | | | | 250 | 300 | | | | | | | |
| | Vol Infused mL | 50 | | | 50 | | 50 | | 50 | | | 50 | | | 50 | |
| ▲ Medication Infusions | | | | | | | | | | | | | | | | |
| Ceftriaxone | 1g IV Q12hr mL | | | | 100 | | | | | | | 100 | | | | |
| Metoclopramide | 10 mg IV QID mL | | | | | 90 | | | | | | | | | | |
| ▲ Other Intake | | | | | | | | | | | | | | | | |
| Oral Intake | mL | | | | | 15 | 100 | | | | | | | | | |
| ▼ Output | | | | | | | | | | | | | | | | |
| Output Total | | 105 | | | | | | | | | | | | | | |
| Urine Voided | mL | | | | | | | | | | | | | | | |
| Urine Catheter | mL | | | | | | | | | | | | | | | |
| ☐ Chest Tubes | | | | | | | | | | | | | | | | |
| Right anterior 20 French | | | | | | | | | | | | | | | | |
| Output | mL | | | | | | | | | | | | | | | |
| Net | | -85 | | | | | | | | | | | | | | |

| Items | | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 | Time Scale | | Actions | | | |
|---|---|---|---|---|---|---|---|---|---|---|---|---|---|---|---|---|---|---|---|---|---|---|
| ▼ Vital Signs | | | | | | | | | | | | | | | | | | | | | | |
| | T (core) degC | 37.2 | | | 37.2 | | 37.2 | 37.2 | 37.2 | 37.2 | 37.2 | 39 | 37.5 | 37.4 | 37.2 | 39 | | | | | | |
| | HR bpm | 88 | | | 88 | | 88 | 92 | 97 | 95 | 86 | 90 | 87 | 87 | 87 | 88 | | | | | | |
| | RR bpm | 20 | | | 20 | | 20 | 16 | 30 | 21 | 29 | 21 | 19 | 20 | 19 | 28 | | | | | | |
| | SBP/DBP Cuff | 102/59 | | | 102/59 | | 102/59 | 101/56 | 101/56 | 99.8/60 | 116/54 | 102/55 | 99.6/58 | 100/58 | 99.2/57 | 110/68 | | | | | | |
| | MAP Cuff | 73 | | | 73 | | 73 | 71 | 71 | 73 | 75 | 71 | 72 | 72 | 71 | 82 | | | | | | |
| | O2 Sat % | 87 | | | 87 | | 87 | 86 | 88 | 86 | 92 | 87 | 86 | 86 | 86 | 46 | | | | | | |
| | Cardiac Rhythm | | | | | | | | | | | | | | | bradyca... | | | | | | |
| ▼ Hemodynamics | | | | | | | | | | | | | | | | | | | | | | |
| | CVP CVP | | | | | | 3 | 4 | 2 | 4 | 4 | 2 | 2 | 4 | 4 | 2 | | | | | | |
| | PAS PAS | | | | | | 27 | 20 | 20 | 5 | 20 | 20 | 20 | 20 | 20 | 20 | | | | | | |
| | PAD PADP | | | | | | 5 | 5 | 5 | 5 | 5 | 5 | 5 | 5 | 5 | 5 | | | | | | |
| ▼ Intake | | | | | | | | | | | | | | | | | | | | | | |
| Intake Total | | 125 | | | | | | | | | | | | | | | | | | | | |
| ☐ Insulin (1 unit/mL) | IV ordered at 2 ... units/hr | 2 | | | 2 | | 2 | 3 | 3 | 2 | 2 | 2 | | | 2 | | | | | | | |
| | Rate mL/hr | 4 | | | 4 | | 4 | 6 | 6 | 4 | 4 | 4 | | | 4 | | | | | | | |
| | Vol Infused mL | 4 | | | 4 | | 4 | 6 | | | | | | | | | | | | | | |
| ☐ Lasix (1...mL) | IV ordered at 0 ... mg/hr | | | | | | | | | | | | | | | | | | | | | |
| | Rate mg/hr | | | | 2 | | 4 | | | | | | | | | | | | | | | |
| | Vol Infused mL | | | | | | | | | | | | | | | | | | | | | |
| ☐ Propofol (10mg/mL) | IV ordered at 8... mcg/kg/min | 50.6 | | | 50.6 | | 50.6 | 50.6 | | 50.6 | | 62.5 | | | 62.5 | | | | | | | |
| | Rate mL/hr | 23.5 | | | 23.5 | | 23.5 | 23.5 | | 23.5 | | 29 | | | 29 | | | | | | | |
| | Vol Infused mL | 23.5 | | | 23.5 | | 23.5 | 23.5 | | 23.5 | | 29 | | | 29 | | | | | | | |
| ☐ Terbutaline (3mcg/kg/min) | IV order... mcg/kg/min | 2 | | | 2 | | 2 | 2 | | 2 | | 2 | | | 2 | | | | | | | |
| | Rate mL/hr | 15 | | | 15 | | 15 | 15 | | 15 | | 15 | | | 15 | | | | | | | |
| | Vol Infused mL | 15 | | | 15 | | 15 | 15 | | 15 | | 15 | | | 15 | | | | | | | |
| ☐ Sodium Chloride 0.45% | ordered at 1 mL/hr | 50 | | | 50 | | 50 | 250 | 50 | | | 50 | | | 50 | | | | | | | |
| | Bolus mL | | | | | | | | 300 | | | | | | | | | | | | | |
| | Vol Infused mL | 50 | | | 50 | | 50 | | | | | 50 | | | 50 | | | | | | | |
| ▲ Medication Infusions | | | | | | | | | | | | | | | | | | | | | | |
| Ceftriaxone | 1g IV Q12hr mL | | | | | | | | | | | 100 | | | | | | | | | | |
| Metoclopramide | 10 mg IV QID mL | | | | | | 100 | | | | | | | | | | | | | | | |
| ▲ Other Intake | | | | | | | | | | | | | | | | | | | | | | |
| Oral Intake | mL | | | | | 15 | | | | | | | | | | | | | | | | |
| ▲ Output | | | | | | | | | | | | | | | | | | | | | | |
| Output Total | | 105 | | | | | | | | | | | | | | | | | | | | |
| Urine Voided | mL | | | | | 90 | | | | | | | | | | | | | | | | |
| Urine Catheter | mL | | | | | | | | | | | | | | | | | | | | | |
| ☐ Chest Tubes | | | | | | | | | | | | | | | | | | | | | | |
| Right anterior 20 French | | | | | | | | | | | | | | | | | | | | | | |
| Output | mL | | | | | | | | | | | | | | | | | | | | | |
| Net | | -85 | | | | | | | | | | | | | | | | | | | | |

| Items | | | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 |
|---|---|---|---|---|---|---|---|---|---|---|---|---|---|---|---|---|---|
| ▼ Vital Signs | | | | | | | | | | | | | | | | | |
| | T (core) | degC | 37.2 | | | 37.2 | | 37.2 | 37.2 | 37.2 | 37.2 | 37.2 | 39 | 37.5 | 37.4 | 37.2 | 39 |
| | HR | bpm | 88 | | | 88 | | 88 | 92 | 97 | 95 | 86 | 90 | 87 | 87 | 87 | 88 |
| | RR | bpm | 20 | | | 20 | | 20 | 16 | 30 | 21 | 29 | 21 | 19 | 20 | 19 | 28 |
| | SBP/DBP Cuff | | 102/59 | | | 102/59 | | 102/59 | 101/56 | 101/56 | 99.8/60 | 116/54 | 102/55 | 99.6/58 | 100/58 | 99.2/57 | 110/68 |
| | MAP Cuff | | 73 | | | 73 | | 73 | 71 | 71 | 73 | 75 | 71 | 72 | 72 | 71 | 82 |
| | O2 Sat | % | 87 | | | 87 | | 87 | 86 | 88 | 86 | 92 | 87 | 86 | 86 | 86 | 46 |
| | Cardiac Rhythm | | | | | | | | | | | | | | | | bradyca... |
| ▼ Hemodynamics | | | | | | | | | | | | | | | | | |
| | CVP | CVP | | | | | | 3 | 4 | 2 | 4 | 4 | 2 | 2 | 4 | 4 | 2 |
| | PAS | PAS | | | | | | 27 | 20 | 20 | 20 | 20 | 20 | 20 | 20 | 20 | 20 |
| | PAD | PADP | | | | | | 5 | 5 | 5 | 5 | 5 | 5 | 5 | 5 | 5 | 5 |
| ▼ Intake | | | | | | | | | | | | | | | | | |
| Intake Total | | | 125 | | | | | | | | | | | | | | |
| ☐ Insulin (1 unit/mL) | IV ordered at 2 ... | units/hr | 2 | | | 2 | | 2 | 3 | 3 | 2 | 2 | 2 | 2 | 2 | 2 | |
| | Rate | mL/hr | 4 | | | 4 | | 4 | 6 | 6 | 4 | 4 | 4 | | | 4 | |
| | Vol Infused | mL | 4 | | 10 | 4 | | 4 | 6 | | | | 4 | | | 4 | |
| ☐ Lasix (1 mg/mL) | IV ordered at 0 ... | mg/hr | | 1910 | | | | 4 | | | | | | | | | |
| | Rate | mg/hr | | | | | | | | | | | | | | | |
| | Bolus | mg | | | | 14 | | | | | | | | | | | |
| | Vol Infused | mL | | | | | | | | | | | | | | | |
| ☐ Propofol (10mg/mL) | IV ordered at 8... | mcg/kg/min | 50.6 | | | 50.6 | | 50.6 | 50.6 | | 50.6 | | 62.5 | | | 62.5 | |
| | Rate | mL/hr | 23.5 | | | 23.5 | | 23.5 | 23.5 | | 23.5 | | 29 | | | 29 | |
| | Vol Infused | mL | 23.5 | | | 23.5 | | 23.5 | 23.5 | | 23.5 | | 29 | | | 29 | |
| ☐ Terbutaline (3mcg/kg/min) | IV order ... | mcg/kg/min | 2 | | | 2 | | 2 | 2 | | 2 | | 2 | | | 2 | |
| | Rate | mL/hr | 15 | | | 15 | | 15 | 15 | | 15 | | 15 | | | 15 | |
| | Vol Infused | mL | 15 | | | 15 | | 15 | 15 | | 15 | | 15 | | | 15 | |
| ☐ Sodium Chloride 0.45% | ordered at 1 | mL/hr | 50 | | | 50 | | 50 | 50 | 50 | | | 50 | | | 50 | |
| | Bolus | mL | | | | | | | 250 | 300 | | | | | | | |
| | Vol Infused | mL | 50 | | | 50 | | 50 | | | | | 50 | | | 50 | |
| ▲ Medication Infusions | | | | | | | | | | | | | | | | | |
| Ceftriaxone | 1g IV Q12hr | mL | | | | | | | | | | | 100 | | | | |
| Metoclopramide | 10 mg IV QID | mL | | | | | 90 | | | | | | | | | | |
| ▲ Other Intake | | | | | | | | | | | | | | | | | |
| Oral Intake | | mL | | | | | 15 | 100 | | | | | | | | | |
| ▲ Output | | | | | | | | | | | | | | | | | |
| Output Total | | | 105 | | | | | | | | | | | | | | |
| Urine Voided | | mL | | | | | 90 | | | | | | | | | | |
| Urine Catheter | | mL | | | | | 15 | | | | | | | | | | |
| ☐ Chest Tubes | | | | | | | | | | | | | | | | | |
| Right anterior 20 French | | | | | | | | | | | | | | | | | |
| Output | | mL | | | | | | | | | | | | | | | |
| Net | | | −85 | | | | | | | | | | | | | | |

| Sherry DeLong  MRN: 009-295  DOB: 9/10/1976  Gender: F  ↻ |
|---|
| Associated Devices |
| ☐ Select All                              X Disassociate  ⌄ |
|  |

2310

| Device Search |
| --- |
| Associate |
| Device: | Sym | 🔍 |

| Device | Details | Vendor | Model |
|---|---|---|---|
| ☐ Symbiq pump | 0 channels | HSPR | Symbiq |
| ☐ Scripted Infuser 21 | 2 channels | CERN | Scripted Infusion |
| ☐ Scripted Infuser 19 | 2 channels | CERN | Scripted Infusion |
| ☐ Scripted Infuser 18 | 2 channels | CERN | Scripted Infusion |
| ☐ Scripted Infuser 17 | 2 channels | CERN | Scripted Infusion |

| | | 13:00 | 12:23 | 12:07 | 12:00 | 11:45 | 11:00 | 10:45 | 10:00 | 09:00 | 08:00 | 07:02 | 07:00 | 06:00 | 05:36 | 05:00 | 04:00 | 03:00 | 02:02 | 02:00 | 01:00 |
|---|---|---|---|---|---|---|---|---|---|---|---|---|---|---|---|---|---|---|---|---|---|
| ▼Vital Signs | | | | | | | | | | | | | | | | | | | | | |
| | Temp Deg C | 37.5 | 38.6 | 37.3 | 37.3 | 37.2 | 37.2 | 38.6 | 37.3 | 38.6 | 37.3 | 37.5 | 37.2 | 38.6 | 37.5 | | | | | | |
| | HR bpm | 80 | 104 | 81 | 80 | 78 | 78 | 104 | 81 | 101 | 81 | 72 | 78 | 104 | 72 | | | | | | |
| | RR bpm | 20 | 20 | 22 | 21 | 18 | 18 | 20 | 22 | 24 | 22 | 20 | 18 | 20 | 20 | | | | | | |
| | SBP/DBP Cuff mmHg | 110/75 | 146/90 | 132/80 | 120/80 | 110/75 | 110/75 | 146/90 | 132/80 | 144/80 | 132/80 | 110/75 | 110/75 | 146/90 | 110/75 | | | | | | |
| | MAP Cuff mmHg | 50 | 73 | 65 | 62 | 50 | 50 | 73 | 65 | 60 | 65 | 50 | 50 | 73 | 50 | | | | | | |
| | SpO2 % | 95 | 99 | 96 | 95 | 97 | 97 | 99 | 96 | 95 | 96 | 97 | 97 | 99 | 97 | | | | | | |
| | Pain Score | 5 | 7 | 3 | 4 | 3 | 3 | 7 | 3 | 8 | 3 | 3 | 3 | 7 | 3 | | | | | | |
| ▼PCA / Epidural | | | | | | | | | | | | | | | | | | | | | |
| Morphine (2 mg) | Basal... mg | | 8 | | | | | 8 | | 8 | | | | 8 | 4 | | | | | | |
| | Clinician Dose mg | | 4 | | | | | 4 | | 4 | | | | 4 | | | | | | | |
| | Patient Dose mg | | 2 | 2 | 2 | 2 | 2 | 2 | 2 | 2 | 2 | | 2 | 2 | | | | | | | |
| | # Attempted | | 2 | 2 | 2 | 2 | 2 | 2 | 2 | 2 | 2 | 2 | 2 | 2 | | | | | | | |
| | # Delivered | | 2 | 2 | 2 | 2 | 2 | 2 | 2 | 2 | 2 | 2 | 2 | 2 | | | | | | | |
| ▼PCA / Epidural Total | | | | | | | | | | | | | | | | | | | | | |

FIG. 26

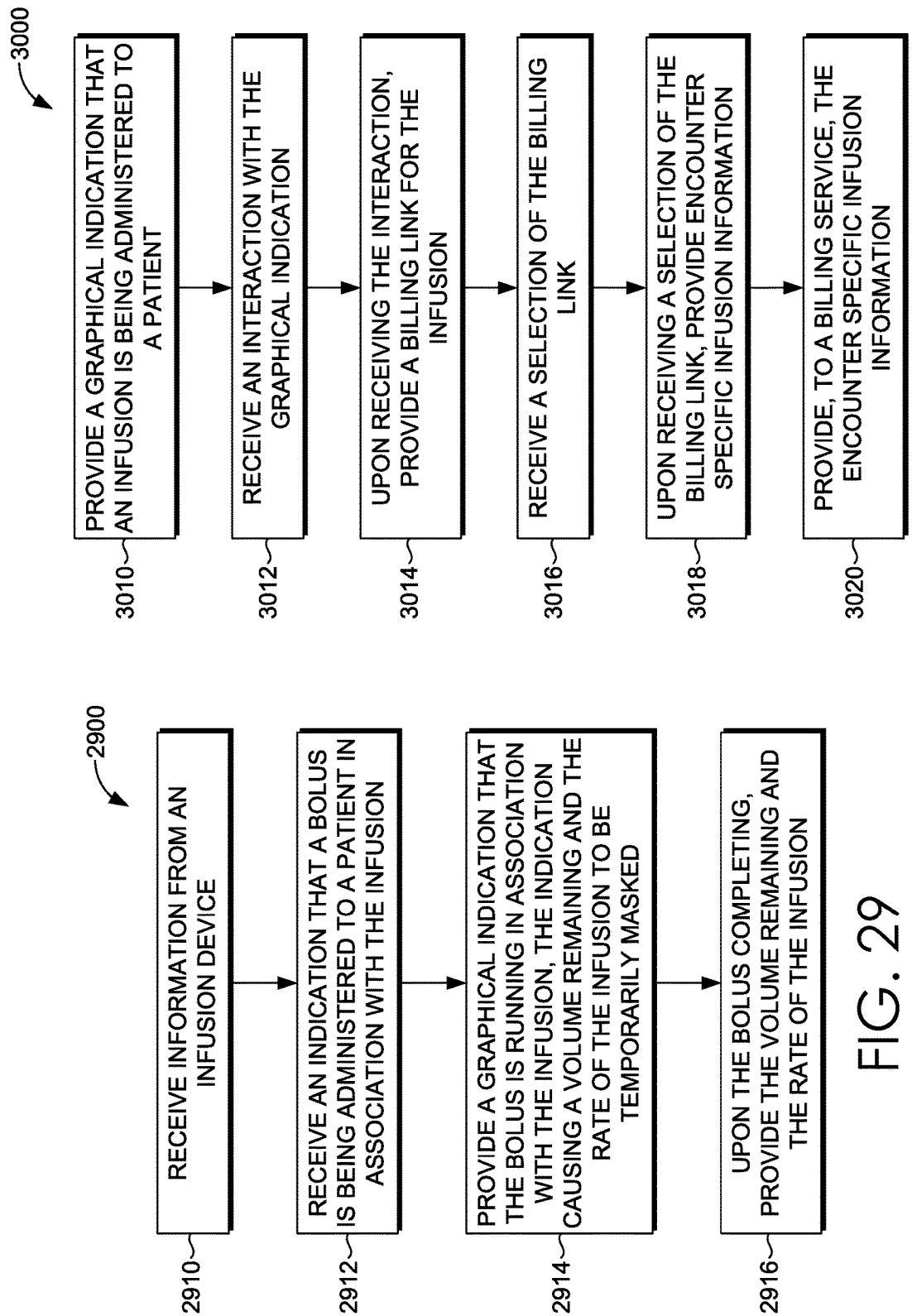

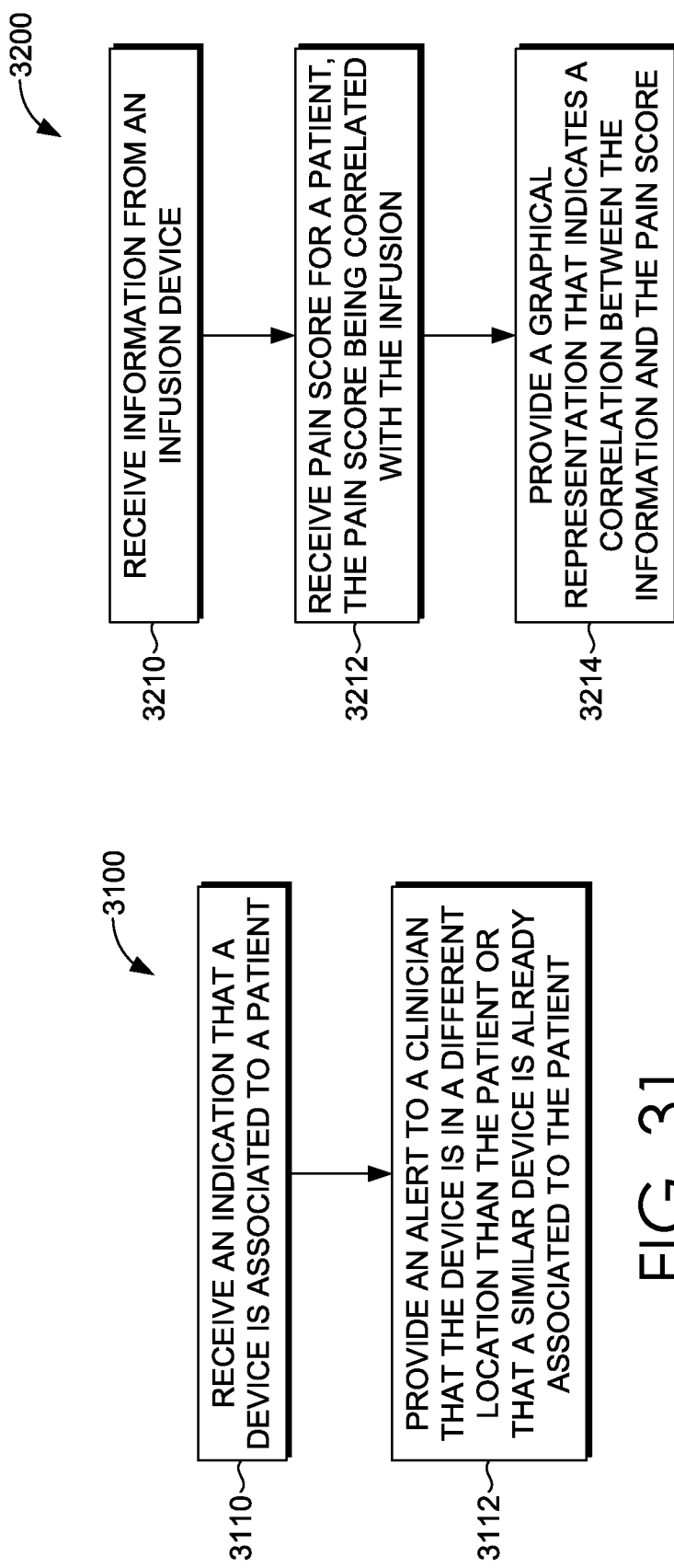

BOLUS DISPLAY AND DOCUMENTATION

CROSS-REFERENCE TO RELATED APPLICATIONS

This Application claims priority to U.S. Provisional Application Ser. No. 62/074,463, filed Nov. 3, 2014, herein incorporated by reference in its entirety, and is related to commonly assigned U.S. Patent Applications entitled "Infusion Billing" U.S. application Ser. No. 14/587,501, "Disassociating Medical Devices" U.S. application Ser. No. 14/587,507, and "Pain Management for Patient Controlled Analgesia and Epidurals" U.S. application Ser. No. 14/587,516, filed concurrently herewith on the same date.

BACKGROUND

Infusion pumps infuse fluids, medications and/or nutrients into the circulatory system of an individual or patient. The infusions may be intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. A bolus is the administration of a discrete amount of medication, drug, or other compound in order to raise its concentration in the blood to an effective level and can be given intravenously or by injection.

Typically, medical devices that are used to treat or care for a patient are not adequately or timely linked to that patient in the patient's record, such as an electronic medical record (EMR). In many instances, these errors in linkage or association may lead to inaccuracies and inconsistencies in treating the patient. Even when the devices are properly associated with a patient, the manual process required to disassociate a device from a patient is often overlooked or forgotten. Data that should be attributed to a new patient utilizing the device remains attributed to the previous patient. This lack of properly and timely disassociating the device results in many inaccuracies and inconsistencies in treating both patients.

SUMMARY

Embodiments of the present invention generally relate to bolus display and documentation. In embodiments, an indication that a bolus is being administered to a patient in association with the infusion is received. A graphical indication the bolus is running is provided, the indication causing a volume remaining and the rate of the infusion to be temporarily masked until the bolus is completed.

Accordingly, in one aspect, an embodiment of the present invention is directed to one or more computer storage media storing computer-useable instructions that, when used by one or more computing devices, cause the one or more computing devices to perform operations. The operations include receiving information from an infusion device, the information including one or more of start time, stop time, duration, rate, dose, or volume of an infusion. The operations also include receiving an indication that a bolus is being administered to a patient in association with the infusion. The operations further include providing, via a user interface, a graphical indication that the bolus is running in association with the infusion, the indication causing a volume remaining and the rate of the infusion to be temporarily masked. The operations also include, upon the bolus completing, providing, via the user interface, the volume remaining and the rate of the infusion.

In another embodiment, an aspect is directed to a computer-implemented method in a clinical computing environment. The method includes receiving information from an infusion device, via a first computing process, the information including one or more of start time, stop time, duration, rate, dose, or volume of an infusion. The method also includes receiving, via a second computing process, an indication that a bolus is being administered to a patient in association with the infusion. The method further includes providing, via a third computing process, a graphical indication that the bolus is running in association with the infusion, the indication causing a volume remaining and the rate of the infusion to be temporarily masked. The method also includes, upon the bolus completing, providing, via a fourth computing process, the volume remaining and the rate of the infusion. Each computing process is performed by one or more computing devices.

A further embodiment is directed to a system comprising: one or more processors; and one or more computer storage media storing instructions that, when used by the one or more processors, cause the one or more processors to: receive information from an infusion device, the information including one or more of start time, stop time, duration, rate, dose, or volume of an infusion; receive an indication that a bolus is being administered to a patient in association with the infusion; provide, via a user interface, an graphical indication that the bolus is running in association with the infusion, the indication causing a volume remaining and the rate of the infusion to be temporarily masked; and upon the bolus completing, provide, via the user interface, the volume remaining and the rate of the infusion.

Embodiments of the present invention generally relate to infusion billing. A graphical indication is provided that indicates an infusion is being administered. Upon an interaction with the user interface being received, a billing link is provided. Once a selection of the billing link is received, encounter specific infusion information is provided. The encounter specific infusion information is provided to a billing service.

Accordingly, in one aspect, an embodiment of the present invention is directed to one or more computer storage media storing computer-useable instructions that, when used by one or more computing devices, cause the one or more computing devices to perform operations. The operations include providing, via a user interface, a graphical indication that an infusion is being administered to a patient, the graphical indication including a volume of the infusion. The operations also include receiving, via the user interface, an interaction with the graphical indication. The operations further include, upon receiving the interaction, providing, via the user interface, a billing link for the infusion. The operations also include receiving, via the user interface, a selection of the billing link. The operations further include, upon receiving a selection of the billing link, providing, via the user interface, encounter specific infusion information including order information, total volume administered, start and end time provided via an infusion device. The operations also include receiving, via the user interface, adjustments to the infusion. The operations further include providing, to a billing service, the encounter specific infusion information.

In another embodiment, an aspect is directed to a computer-implemented method in a clinical computing environment. The method includes providing, via first computing process, a graphical indication that an infusion is being administered to a patient, the graphical indication including a volume of the infusion. The method also includes receiving, via a second computing process, an interaction with the graphical indication. The method further includes, upon receiving the interaction, providing, via a third computing process, a billing link. The method also includes receiving, via a fourth computing process, a selection of the billing link. The method further includes, upon receiving a selection of the billing link, providing, via a fifth computing process, encounter specific infusion information. The method also includes receiving, via a sixth computing process, adjustments to the infusion information, the adjustments includes time adjustments indicating a patient has been moved to another unit of a healthcare facility but is still receiving the infusion from the same bag. Each computing process is performed by one or more computing devices.

A further embodiment is directed to a system comprising: one or more processors; and one or more computer storage media storing instructions that, when used by the one or more processors, cause the one or more processors to: provide, via a user interface, a graphical indication that an infusion is being administered to a patient, the graphical indication including a volume of the infusion; receive, via the user interface, an interaction with the graphical indication; upon receiving the interaction, provide, via the user interface, a billing link; receive, via the user interface, a selection of the billing link; upon receiving a selection of the billing link, provide, via the user interface, encounter specific infusion information including order information, total volume administered, start and end time provided via an infusion device; receive, via the user interface, adjustments to the infusion information indicating a patient has been moved to another unit of a healthcare facility; and provide, to a billing service, the encounter specific infusion information, wherein the billing service separates charges in accordance with a portion of the infusion provided to the patient in each unit of the healthcare facility.

Embodiments of the present invention generally relate to pain management for patient controlled analgesia and epidurals. Information is received from an infusion device. After a pain score or sedation score is documented for a patient, a graphical representation that indicates a correlation between the information and the pain score or sedation score is provided.

Accordingly, in one aspect, an embodiment of the present invention is directed to one or more computer storage media storing computer-useable instructions that, when used by one or more computing devices, cause the one or more computing devices to perform operations. The operations include receiving information from an infusion device, the information including duration, rate, dose, or volume of an infusion and whether the infusion was patient administered, provider administered, or automated. The operations also include receiving a pain score or sedation score for a patient. The operations further include providing, via a user interface, a graphical representation that indicates a correlation between the information and the pain score or sedation score.

In another embodiment, an aspect is directed to a computer-implemented method in a clinical computing environment. The method includes receiving information from an infusion device, via a first computing process, the information including duration, rate, dose, or volume of an infusion and whether the infusion was patient administered, provider administered, or automated. The operations also include receiving, via a second computing process, a pain score or sedation score for a patient. The operations further include providing, via a third computing process, a graphical representation that indicates a correlation between the information and the pain score or sedation score. Each computing process is performed by one or more computing devices.

A further embodiment is directed to a system comprising: one or more processors; and one or more computer storage media storing instructions that, when used by the one or more processors, cause the one or more processors to: receive information from an infusion device, the information including duration, rate, dose, or volume of an infusion and whether the infusion was patient administered, provider administered, or automated; receive a pain score or sedation score for a patient; and provide, via a user interface, a graphical representation that indicates a correlation between the information and the pain score or sedation score.

Embodiments of the present invention generally relate to disassociating medical devices. An indication a device is associated to a patient is received. If the device is in a different location than the patient or a similar device is already associated to the patient, an alert is provided to a clinician.

Accordingly, in one aspect, an embodiment of the present invention is directed to one or more computer storage media storing computer-useable instructions that, when used by one or more computing devices, cause the one or more computing devices to perform operations. The operations include receiving an indication that a device is associated to a patient. The operations also include providing an alert to a clinician that the device is in a different location than the patient or that a similar device is already associated to the patient.

In another embodiment, an aspect is directed to a computer-implemented method in a clinical computing environment. The method includes receiving, via a first computing process, an indication that a device is associated to a patient. The method also includes providing, via a second computing process, an alert to a clinician that the device is in a different location than the patient or that a similar device is already associated to the patient. Each computing process is performed by one or more computing devices.

A further embodiment is directed to a system comprising: one or more processors; and one or more computer storage media storing instructions that, when used by the one or more processors, cause the one or more processors to: receive an indication that a device is associated to a patient; and provide an alert to a clinician that the device is in a different location than the patient or that a similar device is already associated to the patient.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

Embodiments are described in detail below with reference to the attached drawing figures, wherein:

FIGS. 3-28 are screenshots of graphical user interfaces in accordance with embodiments of the present invention;

FIG. 29 is a flow diagram showing a method for bolus display and documentation in accordance with embodiments of the present invention;

FIG. 30 is a flow diagram showing a method for infusion billing in accordance with embodiments of the present invention;

FIG. 31 is a flow diagram showing a method for disassociating devices in accordance with embodiments of the present invention; and FIG. 32 is a flow diagram showing a method for providing pain management for patient controlled analgesia and epidurals in accordance with embodiments of the present invention.

DETAILED DESCRIPTION

Figure 1:
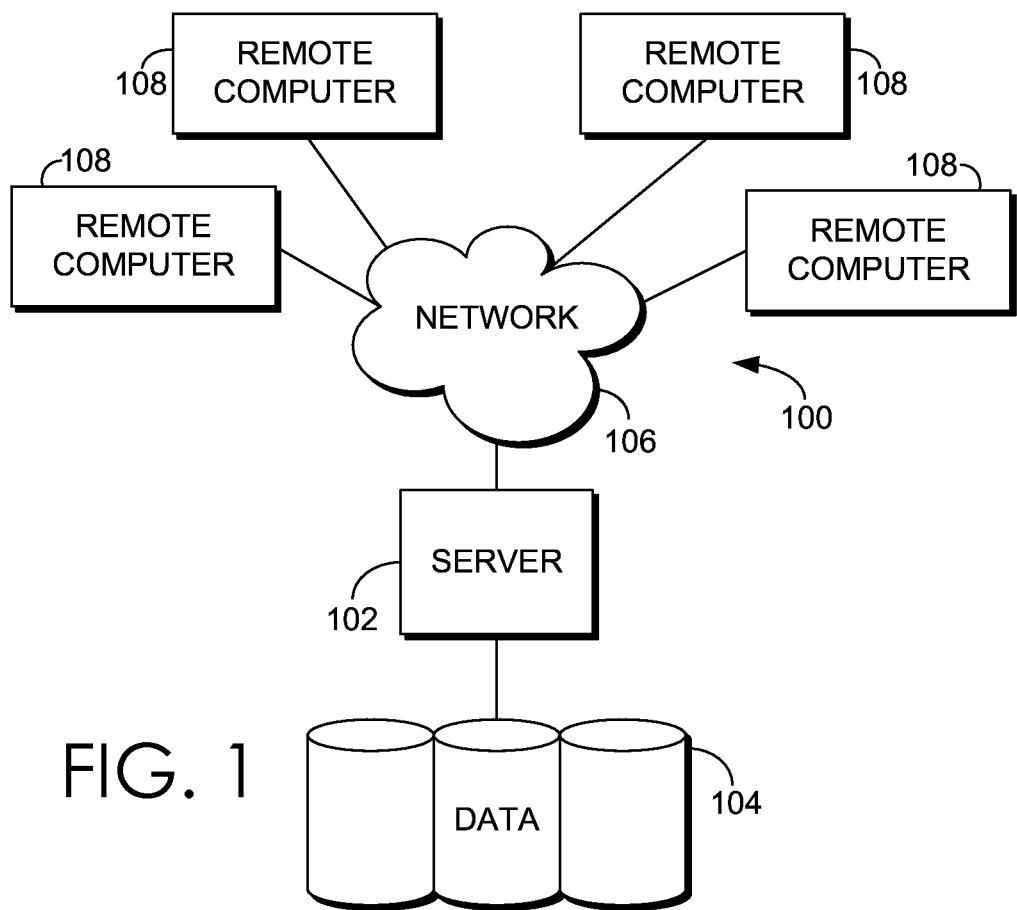
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Current infusion management systems are unable to distinguish between a bolus and an associated infusion. This causes errors when providing an infusion rate and volume remaining because the infusion rate appears abnormally high, as a result, the volume appears abnormally low. Clinicians caring for patients receiving a bolus may be alarmed by the inaccurate infusion rate or prematurely order and make a new and potentially costly infusion bag for the patient.

Embodiments of the present invention are generally directed to methods, computer systems and computer readable media for bolus display and documentation. Information is received from an infusion device that includes one or more of start time, stop time, duration, rate, dose, or volume of an infusion. An indication that a bolus is being administered to a patient in association with the infusion is received. A graphical indication that the bolus is running in association with the infusion is provided via a graphical user interface. The indication causes a volume remaining and the rate of the infusion to be temporarily masked. Upon the bolus completing, the volume remaining and the rate of the infusion is provided via the user interface.

Current infusion billing systems are unable to separate billing events for the same infusion bag. For example, if an infusion bag is initially hung in the emergency department and the patient is moved into acute care and still has the same infusion bag hanging, only one of the departments can bill for the bag. Further clinicians must recall task completion events and determine an encounter type. This results in accounting inaccuracies and prevents one or more of the departments from receiving the appropriate payment.

Embodiments of the present invention are generally directed to methods, computer systems and computer readable media for infusion billing. A clinician is prompted based on encounter, preventing the clinician from having to decide the appropriate encounter type. Start time, stop time, and volume are displayed based on electronic medical record (EMR) and infusion pump data. The order information may also be provided. In this regard, infusion billing documentation may be allowed multiple times for one infusion bag. Consequently, each department may receive the appropriate payment based on the amount of infusion received by the patient in each setting.

Current medical device systems are unable to alert a clinician when a location of the device and a patient do not match. Further, current medical device systems are unable to alert a clinician when the clinician attempts to associate a device to the patient and a similar device is already associated to the patient. Some current systems rely on a device being turned off to determine when the device should be disassociated from the patient. However, many devices, such as cardiac monitors or ventilators, are not typically turned off and the current systems are unable to determine when these devices should be disassociated. This results in an inaccurate flow of data from the device to the EMR of the patient and may cause a clinician to make errors in the diagnosis and/or treatment of the patient. Further, it is not uncommon to have pumps that have primary and secondary associations. Current systems do not allow association or programming of secondary pumps if they are hung as primary.

Embodiments of the present invention are generally directed to methods, computer systems and computer readable media for disassociating devices. Alerts are provided when a device is associated to a patient but is not in the same location as the patient. Similarly, alerts are provided if more than one device of the same subcategory is associated to the patient. Characteristics of the pump may be identified to determine if the pump is infusing the medication as a secondary or primary and allow for flexing of the bag type. These characteristics are provided to the front end application to make the appropriate association.

Current infusion management systems are unable to provide a correlation between pain score or sedation score and patient controlled analgesia and epidurals. This prevents a clinician from determining when the clinician needs to increase a dosage, provide more medication, or educate the patient in how the patient may administer additional medication.

Embodiments of the present invention are generally directed to methods, computer systems and computer readable media for providing pain management for patient controlled analgesia and epidurals. Information is received from an infusion device that includes duration, rate, dose, or volume of an infusion and whether the infusion was patient administered, provided administered, or automated. After a pain score or sedation score is documented for a patient, a graphical representation is provided, via a user interface that indicates a correlation between the information and the pain score or sedation score.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, students, office assistants and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
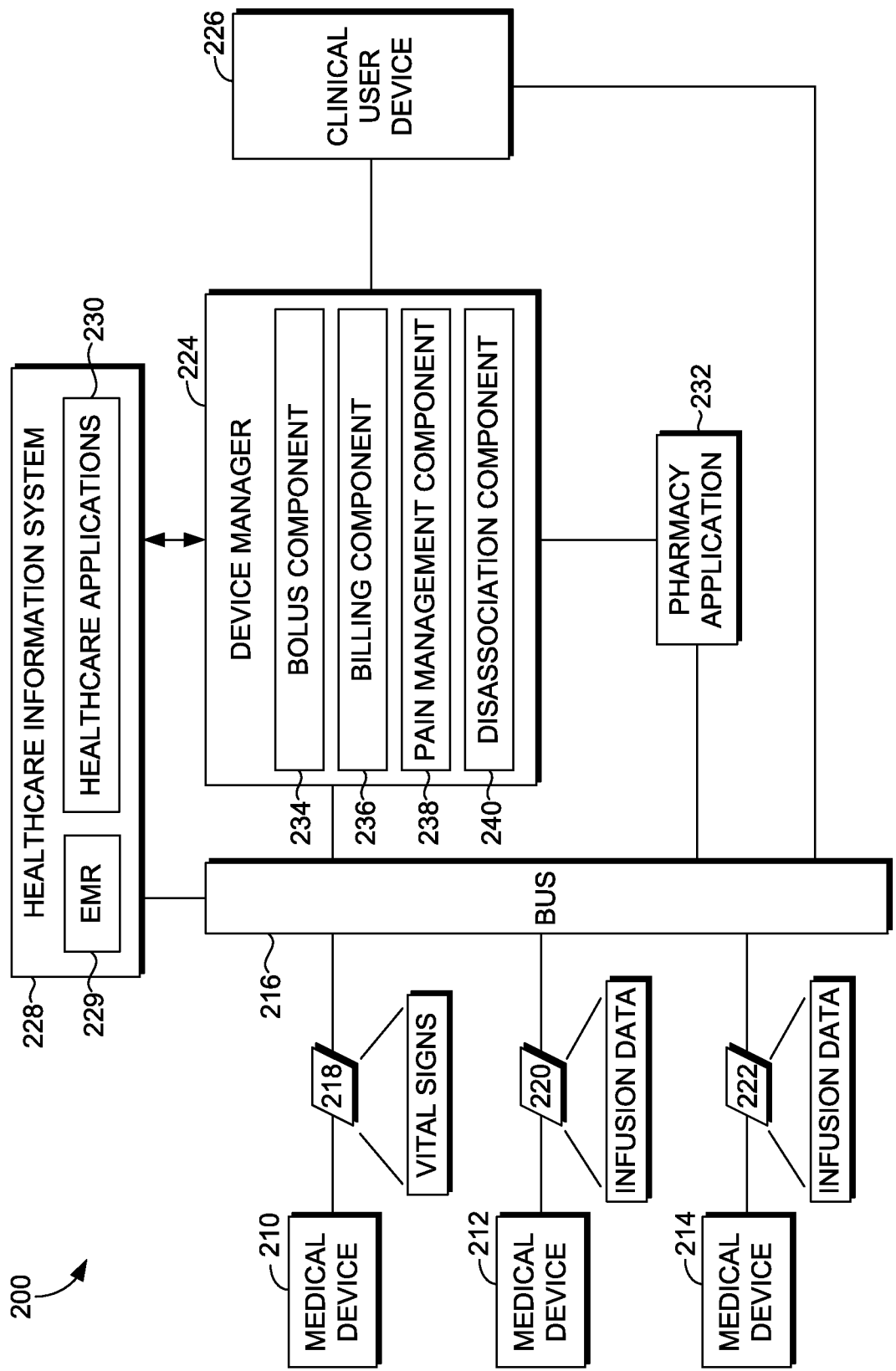
FIG. 2 is an exemplary system architecture suitable to implement embodiments of the present invention.

Turning now to FIG. 2, a schematic diagram depicts an operating environment, identified generally by reference numeral 200, suitable to practice an embodiment of the present invention. FIG. 2 includes various components that communicate with one another, including medical device 210, infusion pump devices 212 and 214, communication devices 226, bus 216, device manager 224, healthcare information system 228 and infusion application 232. In one embodiment of the present invention, data generated by a medical device 210 or an infusion pump device 212, and 214 is routed to and managed by device manager 224, as opposed to, each medical device 210 and infusion pump device 212 displaying information on the medical device or infusion pump respectively. For example, data 218, 220, and 222 is communicated to bus 216, which might then forward the data to device manager 224 to be further processed and routed. Before describing in more detail how these components communicate, each component will be generally described.

In an embodiment of the present invention, medical device 210 might include cardiac monitors, ventilators, balloon pumps, patient beds, sequential-compression devices, electronic security devices, and vital-sign detecting devices. Medical device 210 may generate various data (e.g., measured heart rate) that, as described in more detail below, is communicated to other components (e.g., bus 216) of operating environment 200. Moreover, medical device 210 might also receive information from components of operating environment 200.

In another embodiment of the present invention infusion pumps 212 and 214 infuse fluids, medications and/or nutrients into the circulatory system of an individual or patient. The infusions may be, but are not limited to, intravenous, subcutaneous, arterial, epidural and the like. Infusion pumps can administer injections continuously, intermittently, or upon patient request. Infusion pumps are used by clinicians for patients when more accuracy is needed than with manually adjusted gravitational administration of fluids into a patient's circulatory system. Infusions pumps can be used for infusion of a variety of fluids and medications including, but not limited to anesthesia, chemotherapy, IV drugs, blood transfusions and the like. The fluid, medication and/or nutrients are typically contained in an infusion container, such as an infusion bag. It will be appreciate that any type container may be utilized to hold the infusion fluid, medication and/or nutrients. Infusion pumps 212 and 214 generate various data, including, but not limited to, remaining volume of infusion (e.g., amount remaining in fluid container), rate of infusion (e.g., how fast fluid is being infused), alerts (e.g., air in line, maintenance of pump needed, high backpressure, low infusion, occlusion, or pump stopped). This data is communicated to other components (e.g., bus 216) of operating environment 200. Moreover, infusion pumps 212 and 214 might also receive information from components of operating environment 200.

Healthcare information system 228 includes an integrated system of healthcare-related information that is usable by a healthcare facility to operate and provide patient care. For example, healthcare information system 228 includes an electronic medical record 229 (also referred to herein as "EMR") and a healthcare applications component 230. EMR 229 includes an electronic version of patient records including information for the patient, such as medication and infusion orders, tasks, images, examination reports, testing and lab results, medical history, etc. Healthcare applications component 230 includes information that is input and provided at a patient's point-of-care (e.g., patient bedside) to assist healthcare professionals to provide appropriate care. An exemplary applications component 230 includes a patient order entry component for entering electronic healthcare orders for a patient. In an embodiment of the present invention, healthcare information system 228 receives information from other components, as will be described in more detail below. Moreover, healthcare information system 228 might also provide information that is communicated to other components of operating environment 200.

Communication devices 226 include devices that are used within a healthcare facility to receive, display and send information to a user, such as a clinician. Communication devices 226 also facilitate requests to receive additional information. Exemplary communication devices 226 include personal communication devices, a clinician computer workstation, and an email system. Personal communication devices include devices that are used by an individual to receive and send information, such as an in-house phone, a pager, and a mobile device. Workstations include a remote computer terminal that is used to present information to a user, such as a clinician, and receive input. Workstations might be set up at a nurse's station to or at a patient bedside. Accordingly, in an embodiment of the present invention, communication devices 226 present to users information that is received from other components of operating environment 200. Moreover, communication devices 226 might also receive inputs from a clinician that are communicated to other components of operating environment 200. Communication devices 226 also communicate to other components of operating environment 200 requests to receive additional information. For example, personal communication device 246 might communicate information to device manager 224, HIS, 228 EMR 229, infusion application 232 and medical devices 210, 212 and 214.

Infusion application 232 is an electronic application for receiving medication orders, such as infusion orders, to be filled or displayed. An exemplary infusion system is CareAware Pharmacy Management by Cerner Corporation, Kansas City Mo. In a pharmacy setting, orders for medications, fluids and nutrients to be filled by a pharmacist are displayed in the pharmacy or pharmacy IV room. The pharmacist can use this information to drive the pharmacy workflow and make sure the necessary medication orders are filled. In another embodiment, infusion application 232 may be an automated pharmacy dispensing system such as Cerner RXStation by Cerner Corporation of Kansas City, Mo. The automated pharmacy system may be an apparatus pre-loaded with medication, fluids and/or nutrients that may be dispensed to fill patient orders. As can be appreciated, the infusion application 232 may be any application that allows a clinician to view or interact with any of the bolus data described herein. Similarly, the infusion application 232 may be any application that allows a clinician to view or interact with device associations as described herein.

As previously indicated, and as depicted in FIG. 2, each of medical devices 210, infusion pumps 212 and 214, healthcare information system 228, communication devices 226 and infusion application 232 may be in communication with bus 216. Bus 216 generally provides a connection framework for these components by creating and managing all connections, providing a messaging architecture to facilitate an exchange of information between the various components of FIG. 2, and providing general operational and management capabilities for connected devices. In one embodiment, medical device 210, infusion pumps 212 and 214, communication devices 226, healthcare information system 228 and infusion application 232 communicate with bus 216 as described in U.S. patent application Ser. No. 12/347,475 (U.S. Pat. App. '475), which is incorporated herein by reference. For example, infusion pumps 212 and 214 might include various different types of infusion pumps that are manufactured by various different vendors. As such, components of FIG. 2 might communicate with bus 216 via a gateway (e.g., device gateway or internal gateway), an adapter, or by any other means described by U.S. Pat. App. '475. In a further embodiment, bus 216 includes those capabilities described in U.S. Pat. App. '475. As indicated in U.S. Pat. App. '475, once data is received (e.g., data 218, 220, 222, and 227) it can be sorted and routed to other applications.

In an embodiment of the present invention, such applications are included in a device manager 224. As such, bus 216 might receive information (e.g., data 218, 220, and 222) and route the data to device manager 224. Moreover, bus 216 might receive information from communication devices 226 and route the information to device manager 224. In a further embodiment, bus 216 receives information from healthcare information system 228 and routes the information to device manager 224. In another embodiment, bus 216 receives information from device manager 224 and routes the information to other components. For example, bus 216 routes information from clinician devices 226 to healthcare information system 228.

In an embodiment of the present invention, device manager 224 communicates with bus 216 and functions to consolidate and manage information received from the various components of operating environment 200. In this embodiment, instead of components communicating directly with one another, information is routed through and processed by device manager 224. Device manager 224 allows for consolidation and communication of information from various sources, which may not easily integrated or combinable by direct communication. For example, device manager 224 allows for information from infusion pumps 212 and 214 to be packaged with information from medical device 210, healthcare information system 228 and infusion application 232 in order to generate and communicate a more information-rich notification to a notification recipient (e.g., personal communication device 246). Moreover, a set of normalized information is more easily sorted and reported than a set of information that organized in alternative formats of various information sources. Alternatively, medical device 210, infusion pumps 212 and 214, infusion application 232, clinician user devices 226 and healthcare information system 228 may communicate directly with device manager via a network environment.

Device manager 224 communicates with bus 216 and functions to document, display and manage infusion information received from infusion pumps 212 and 214. Device manager includes bolus component 234, billing component 236, pain management component 238, and disassociation component 240. While these components are included in the embodiment of FIG. 2, any number of components, either more or less than the illustrated components, may be used to accomplish the purposes of the present invention. Other components and subcomponents are contemplated to be within the scope of the present invention. Furthermore, although depicted as residing on one device, such as a server, it will be appreciated that any number of components and/or subcomponents may reside on any number of computing devices or servers.

Device manager 224 associates the infusion pump and/or pump channel for a patient and an order for a patient in response to receiving an indication that the infusion pump and patient order are to be associated. In one embodiment, if the infusion pump is a multi-channel infusion pump, an order for a patient may be associated with the pump and the particular channel utilized for administration of the ordered medication, fluid and/or nutrient. For example, a first order for a first medication is associated with first channel of a multi-channel pump and a second order for a second, and different, medication for the same patient associated with a second channel of a multi-channel pump.

In one embodiment, identifications of the patient, infusion pump and channel are received. The identifications may be received in a number of ways, including, but not limited to, scanning a barcode associated with the patient, pump and/or channel, entering a name or identification associated with the patient, pump and/or channel or searching an electronically searchable database for a patient, pump and/or channel.

This indication to associate an infusion pump and/or channel and patient order may take many forms. An order is an instruction or request for a procedure, a medication, infusion fluid, nutrients, a laboratory test, an evaluation, a treatment, or a nursing task to be performed for a patient. An explicit association may be available to the user, such as through a selectable button on a graphical user interface displayed on the user device. The patient order, infusion pump and/or channel may be associated prior to, simultaneously with of after receiving data from an infusion pump and/or channel. Device manager 224 may suggest orders to associate with one or more infusion pumps and/or channels. For example, device manager 224 may filter patient orders to display only orders to be administered by infusion pump.

Device manager 224 acquires or receives data from an infusion pump and associated channel that has been associated with a patient and/or order for the patient. The type of data that may be received include information regarding volume of fluid infused, volume of fluid remaining to be infused, rate of infusion and alerts, as well as information associated with the administration of a bolus, as described herein. Device manager 224 may also receive data from medical devices other than infusion pumps, such as vital sign and blood pressure monitors. The data is in computerized form and is communicated in electronic form to the BUS and/or event manager without any user intervention. For example, the device would automatically be sent to the BUS and/or device manager without a user, such as a nurse or clinician, having to manually key-in or enter any information into a computer system.

In one embodiment, the data received from the infusion pumps and medical devices can be manipulated (e.g., by a clinician) prior to being stored in the patient's EMR. The data may be stored in an application or service such that a user can edit the data prior to the data being transmitted to the patient's EMR. Device manager 224 continually receives data from the associated infusion pumps and medical devices as long as they are associated to the patient and/or patient's order. A continuous feed of data may be fed from the infusion pump and/or medical device to bus 216 and then to device manager 224.

Device manager 224 determines the status of the device based on data received from an infusion pump. The status may include whether or not a device is connected to the system or if it has lost connectivity, whether a pump is infusing or has been stopped, volume of fluid remaining to be dispensed, rate of infusion and maintenance information. In one embodiment, if the device manager 224 does not receive any data from an infusion pump (e.g., such as a heartbeat signal of the device or any other data) it will be determined that the infusion pump has lost connectivity.

In another embodiment, device manager 224 may not receive any information about rate or volume remaining but still receives an indication given at a certain interval of time that a particular infusion pump is connected to bus 216. Based on this data, device manager 224 determines that the infusion has been stopped but the infusion pump is still connected. Device manager 224, if needed, also performs any necessary conversions on the data received from the infusion pump needed to determine the rate of infusion, volume remaining to be infused based on data received from an infusion pump or type of alert needed. In addition, device manager 224 can rate the alert information received from the infusion pump and determined by level of severity. The level of severity may be represented by an icon displayed for the alert.

Device manager 224 displays and communicates data to the user devices 226 and can receive user inputs from a user device 226. The user devices 226 are separate devices from the medical device 210 and infusion pumps 212 and 214. Device manager 224 can display a variety of information received from an infusion pump in a variety of formats. Device manager 224 displays an identification of a medical device an associated order for a patient. In addition, device manager 224 may display available infusion pumps, pump channels and patient orders to be associated.

Textual information regarding the rate of infusion of the infusion pump, the volume infused and the volume remaining to be infused may be displayed to a clinician. Textual information regarding the status of the infusion pump generated by device manager 224 may also be displayed. Patient information from the patient's EMR includes details of the order associated with the infusion pump and/or channel, patient identification and demographic information. In addition, device manager 224 may provide data received from an infusion pump in a format such that it may be graphed against time on graphical user interface for display to a clinician.

By selecting a protocol via the device manager 224, the appropriate data is displayed and if desired, transmitted to the patient's EMR. This avoids the onerous and time-consuming task of requiring a clinician to manually collect and record data, or manually alter collection and recordation times. Accordingly, the clinician is able to spend more time caring for the patient and less time reviewing and fulfilling requirements associated with each individual patient's order.

Bolus component 234 receives information from an infusion device. The information includes one or more of start time, stop time, duration, rate, dose, or volume of an infusion. Bolus component 234 receives an indication that a bolus is being administered to a patient in association with the infusion. The indication may be received via the infusion device or based on a clinician interaction with a user interface. Bolus component 234 provides, via the user interface, a graphical indication that the bolus is running in association with the infusion. The indication causes a volume remaining and the rate of the infusion to be temporarily masked. Upon the bolus completing, bolus component 234 provides, via the user interface, the volume remaining and the rate of the infusion.

Billing component 236 provides, via a user interface, a graphical indication that an infusion is being administered to a patient. The graphical indication includes a volume of the infusion. Billing component 236 receives, via the user interface, an interaction with the graphical indication. Upon receiving the interaction, billing component 236 provides, via the user interface, a billing link. Billing component 236 receives, via the user interface, a selection of the billing link. Upon receiving a selection of the billing link, billing component 236 provides, via the user interface, encounter specific infusion information. The encounter specific information includes order information, total volume administered, start and end time provided via an infusion device. Billing component 236 receives, via the user interface, adjustments to the infusion information. Billing component 236 provides, to a billing service, the encounter specific infusion information.

Pain management component 238 receives information from an infusion device. The information includes duration, rate, dose, or volume of an infusion. The information further includes whether the infusion was patient administered, provided administered, or automated. Pain management component 238 receives a pain score or sedation score for a patient. Pain management component 238 provides, via a user interface, a graphical representation that indicates a correlation between the information and the pain score or sedation score.

Disassociation component 240 receives an indication that a device is associated to a patient. The device may be any type of medical device and is not limited to infusion pumps. Instead it is contemplated that the device may include devices that are not typically turned off, such as cardiac monitors and ventilators. Disassociation component 240 may also distinguish between primary and secondary devices and disassociate a secondary device so it may be associated and programmed as a primary device. Disassociation component 240 provides an alert to a clinician that the device is in a different location than the patient or that a similar device is already associated to the patient.

For example, healthcare resources such as clinicians, patients, equipment, clinical devices, and the like may be tracked via a plurality of sensors in the healthcare environment. The sensors in the healthcare environment may utilize ultrasound technology, infrared technology, radio-frequency identification technology, and the like. Using said technology, the sensors send out signals to clinician identifiers, patient identifiers, item identifiers, clinical device identifiers, or the like. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier and, thus, are aware of the resources within the healthcare environment. The respective identifiers associated with the resources may be located, e.g., on the person, on the item, or on the device. Exemplary identifiers include badges, wristbands, tags, and the like. The locations of clinicians, patients, equipment, or the like, associated with a responding identifier, is presented or displayed on the dashboard.

If the signals indicate that the patient and a particular device that is associated with the patient are in two different locations, an alert is provide to prevent data from the device being communicated to the EMR of the wrong patient. Similarly, if a clinician attempts to associate a device to the patient, and that patient is already associated to a similar device, the clinician is alerted. In another example, if a clinician attempts to associate a device to the patient that conflicts with another device the patient is already associated to, a diagnosis of the patient, or a treatment the patient is receiving, the clinician is alerted.

Figure 3:
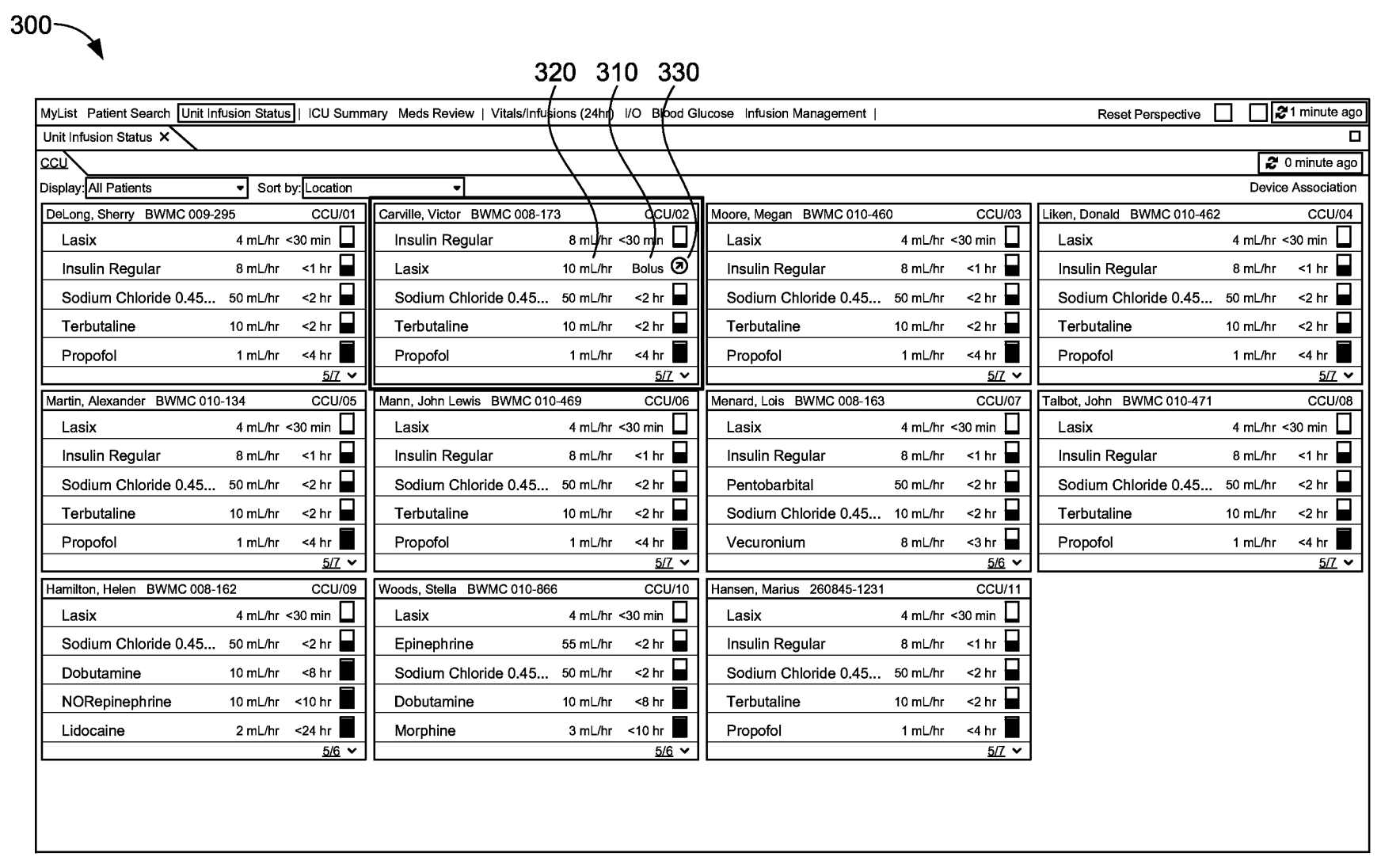

Turning now to FIG. 3, an illustrative graphical user interface 300 is shown for a nurse manager view of infusions, in accordance with an embodiment of the present invention. As illustrated, a bolus 310 is running for one of the patients. Instead of showing a calculated length of time remaining for the bolus, the time remaining is masked and replaced with an indicator for the bolus 310. Similarly, instead of showing the current rate of the infusion (that includes the bolus), the ordered rate of infusion 320 is shown. This prevents the clinician from seeing a very high rate that is caused by the bolus. Also, rather than show a graphical indicator for the amount of fluid remaining, an arrow 330 indicates that a bolus is running. This prevents the graphical indicator from making it appear the fluid remaining is nearly empty based on the high rate associated with the bolus. The arrow 330 may be color coded to indicate the amount remaining so the clinician will know if a bag needs to be replaced once the bolus is complete.

Turning now to FIG. 4, an illustrative graphical user interface 400 is shown for an individual view of infusions, in accordance with an embodiment of the present invention. As illustrated, the calculated dose rate 410 is not populated while the bolus is running. Similarly, the time remaining is replaced with an indicator for the bolus 420. Because a distinction is made when a bolus is being administered to a patient, errors related to the infusion rate and volume remaining can be prevented. For example, the indicator prevents the infusion rate from appearing abnormally high and the volume remaining from appearing abnormally low. In this regard, clinicians caring for patients receiving a bolus will not be alarmed by inaccurate infusions rates or prematurely order and make new and potentially costly infusion bags.

Turning now to FIG. 5, an illustrative graphical user interface 500 is shown for a pharmacy view of infusions, in accordance with an embodiment of the present invention. As illustrated, the time remaining 510 is replaced with an indication 510 a bolus is running. It is estimated that there is approximately thirty to forty percent error rate in making infusion bags which can be extremely expensive. In many cases, once a bag has been made, it cannot be reused. In large part, this is based on a pharmacist seeing the time remaining artificially low based on a bolus being administered when, in reality, the infusion bag still has sufficient fluid and time remaining. Accordingly, the error rate is greatly reduced in accordance with the features described herein.

Figure 6:

Turning now to FIG. 6, an illustrative graphical user interface 600 is shown for a plurality of infusions, in accordance with an embodiment of the present invention. A bolus row 610 has been added indicating the patient has been administered two boluses 612, 614 at a time corresponding to when the bolus completed. The bolus row may be created based on a communication from the infusion device. If the infusion device is unable to communicate the information necessary to create the bolus row, the bolus row may be created manually, as described below. The bolus row includes an amount of the bolus administered to the patient. The bolus row may be associated with a medication and positioned adjacent to a corresponding infusion.

Figure 7:
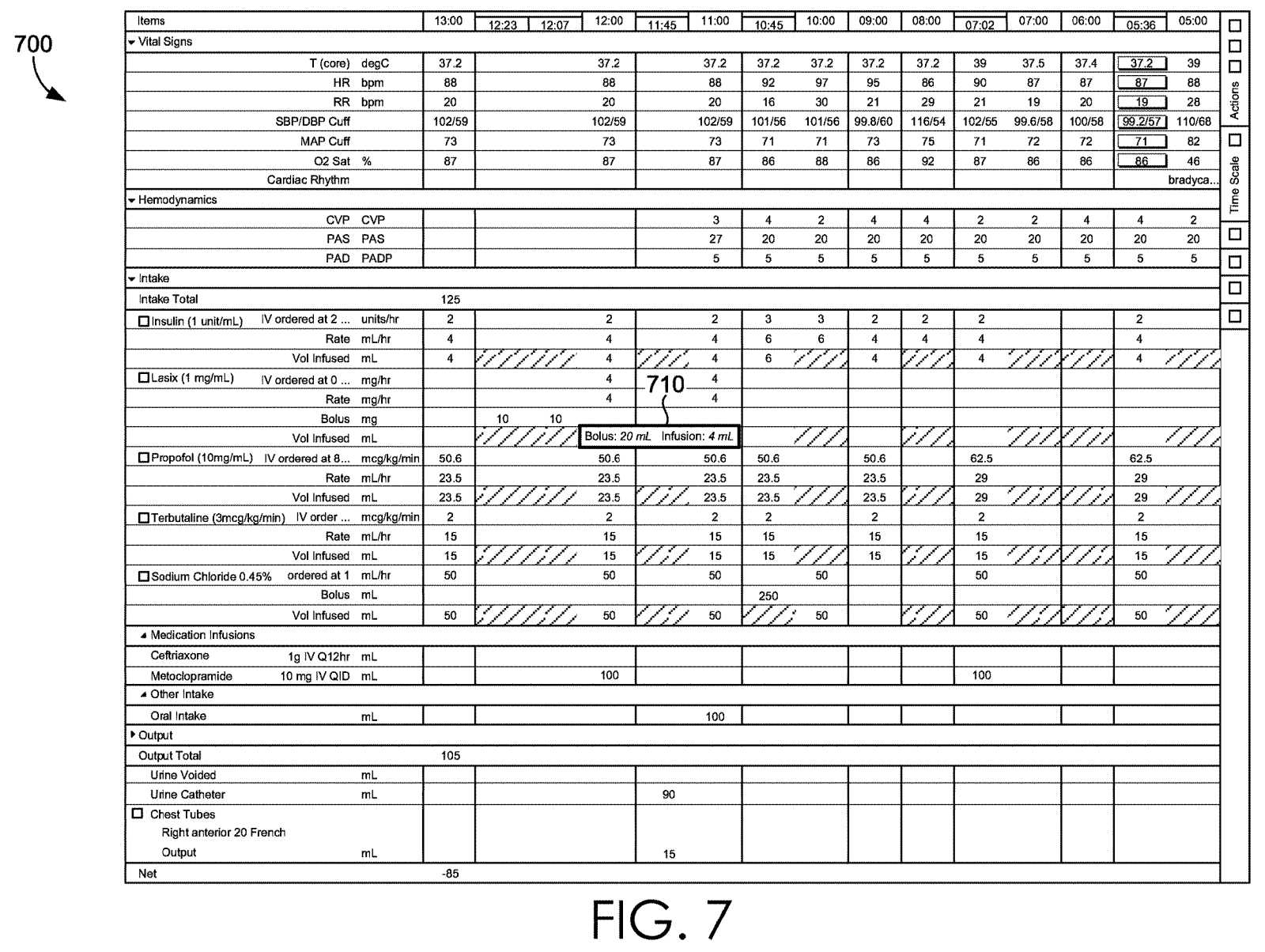

Turning now to FIG. 7, an illustrative graphical user interface 700 is shown for a plurality of infusions, in accordance with an embodiment of the present invention. Upon an interaction with the total volume of the infusion, a dialogue box 710 opens and identifies an amount of the bolus and an amount of the infusion.

Figure 8:
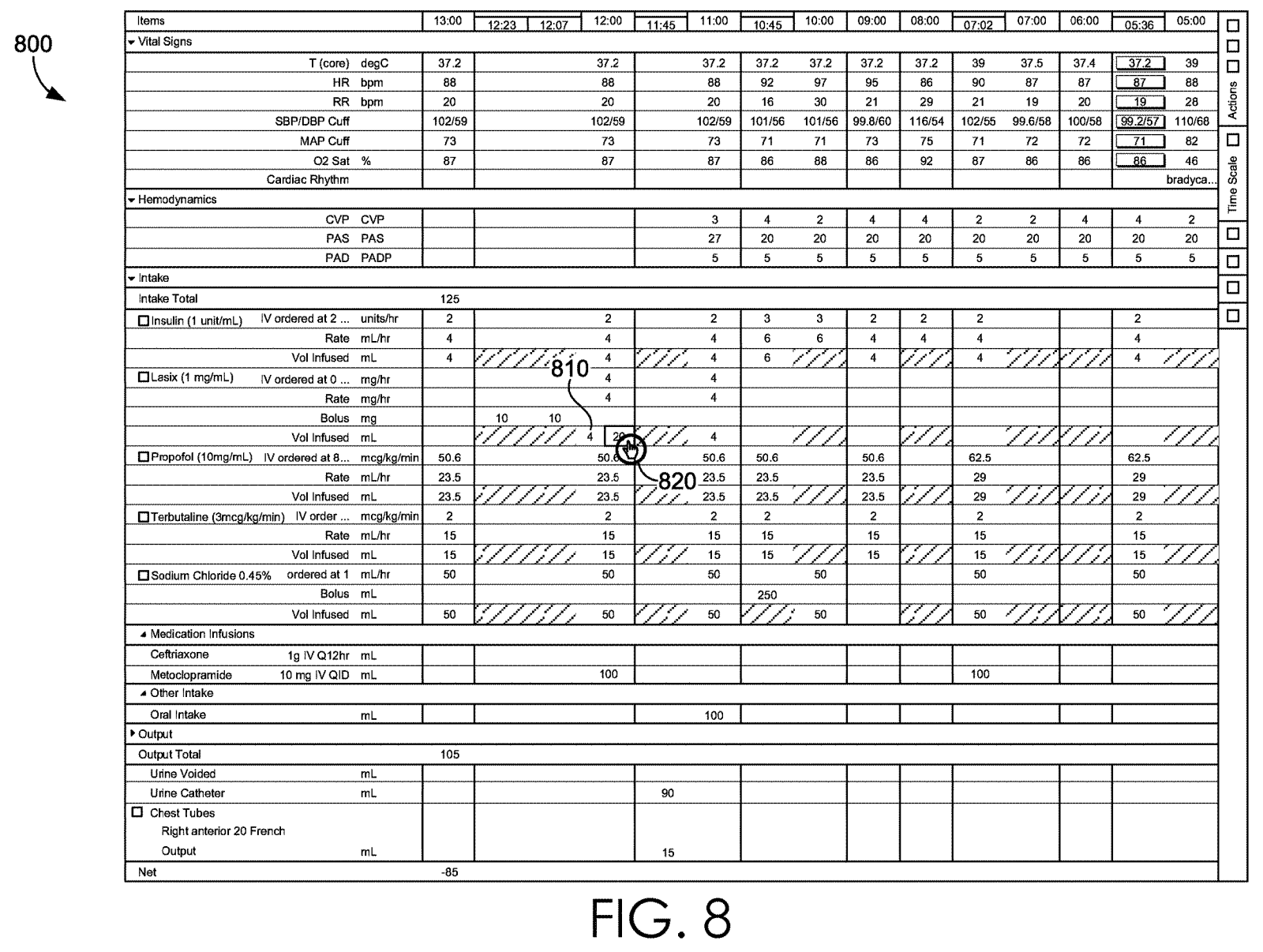

FIG. 8 is an illustrative graphical user interface 800 showing a plurality of infusions, in accordance with an embodiment of the present invention. The volume infused by infusion 810 and bolus 820 is indicated separately. The infusion volume 810 and bolus volume 820 may have a different appearance (e.g., color, typeface, size, and the like) indicating that they have not been signed by a clinician. Once the bolus is signed, the associated bolus volume 810 is also signed.

FIG. 9 is an illustrative graphical user interface 900 showing a plurality of infusions, in accordance with an embodiment of the present invention. Upon an interaction with the total volume of the infusion, a dialogue box 910 opens and identifies an amount of the bolus and an amount of the infusion.

Figure 11:
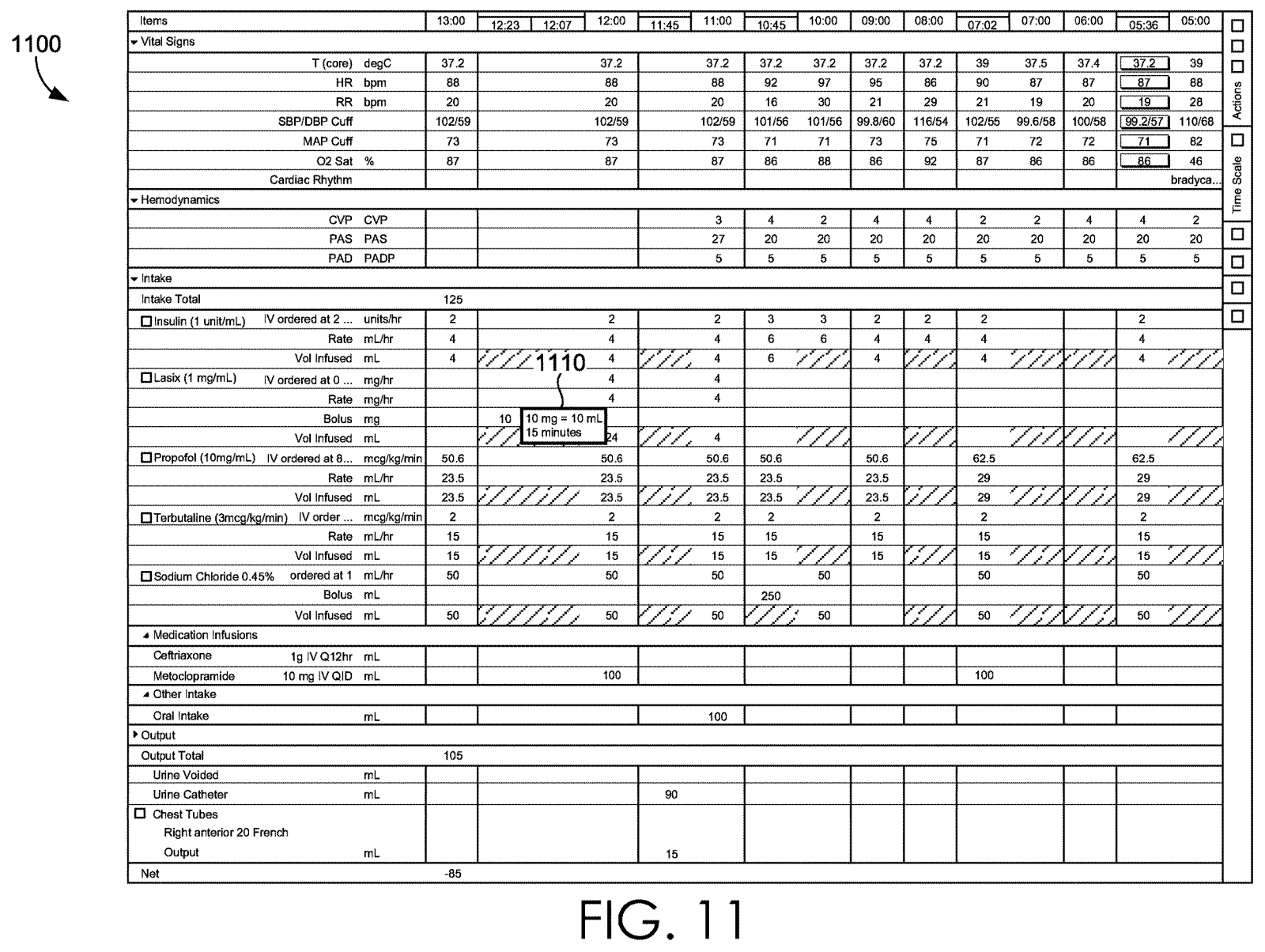

FIGS. 10 and 11 are graphical user interfaces 1000, 1100 showing a plurality of infusions, in accordance with embodiments of the present invention. Interacting with the bolus row 1010 causes a dialogue box 1110 to open that indicates the strength of the bolus as well as the volume. Similarly, the duration of the bolus is calculated and provided by the dialogue box 1110.

Figure 13:
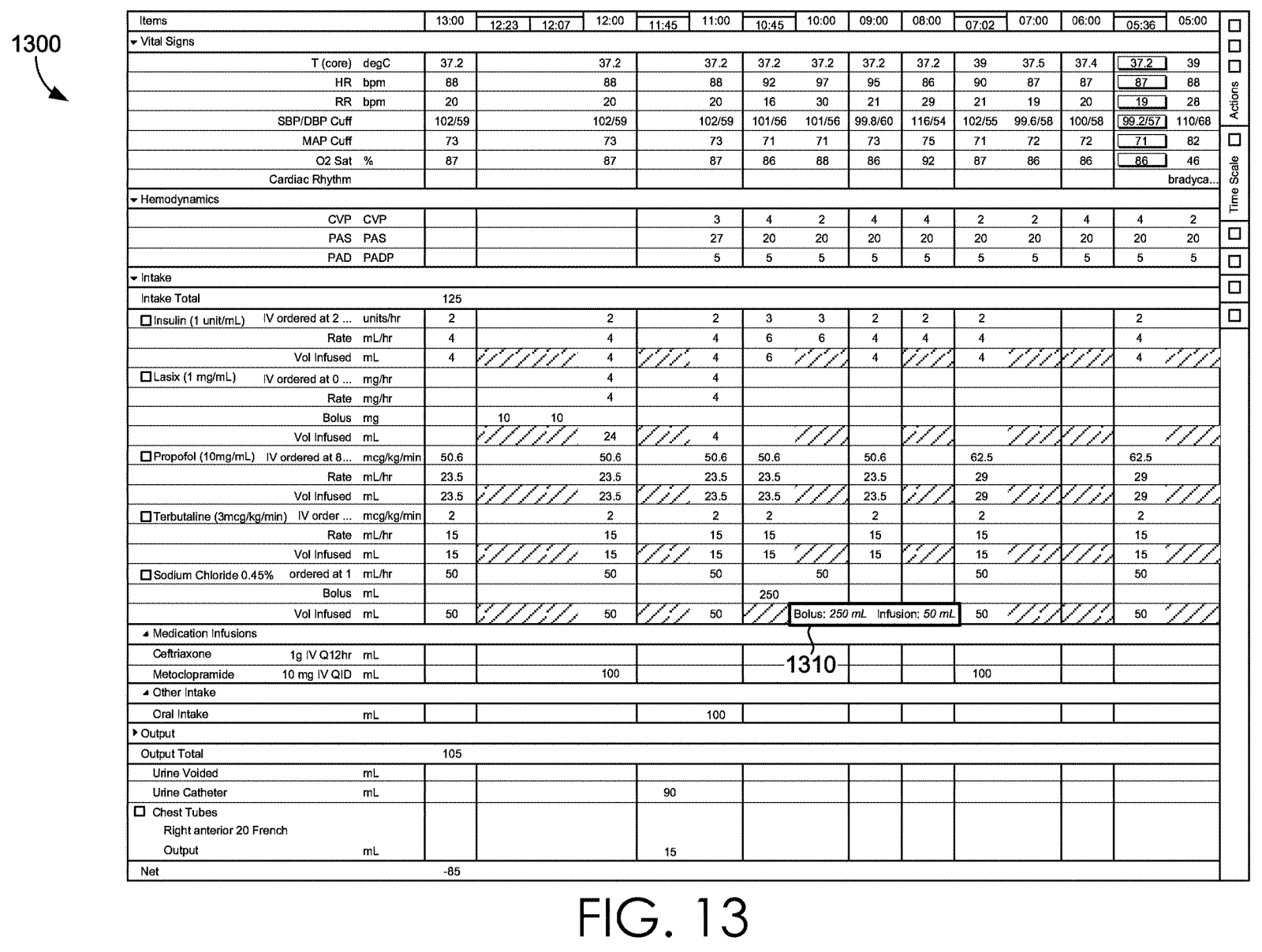

Turning to FIGS. 12 and 13, illustrative graphical user interfaces 1200 and 1300 of a plurality of infusions is shown, in accordance with embodiments of the present invention. A bolus row 1210 has been added indicating the patient has been administered a bolus 1230. The unit of measure is mL indicating a fluid bolus. The total volume infused 1220 and the volume of the infusion 1240 is also provided. Upon interacting with the total volume 1220, a dialogue box 1310 opens revealing a breakdown of the amount of bolus and the amount of infusion.

Figure 14:
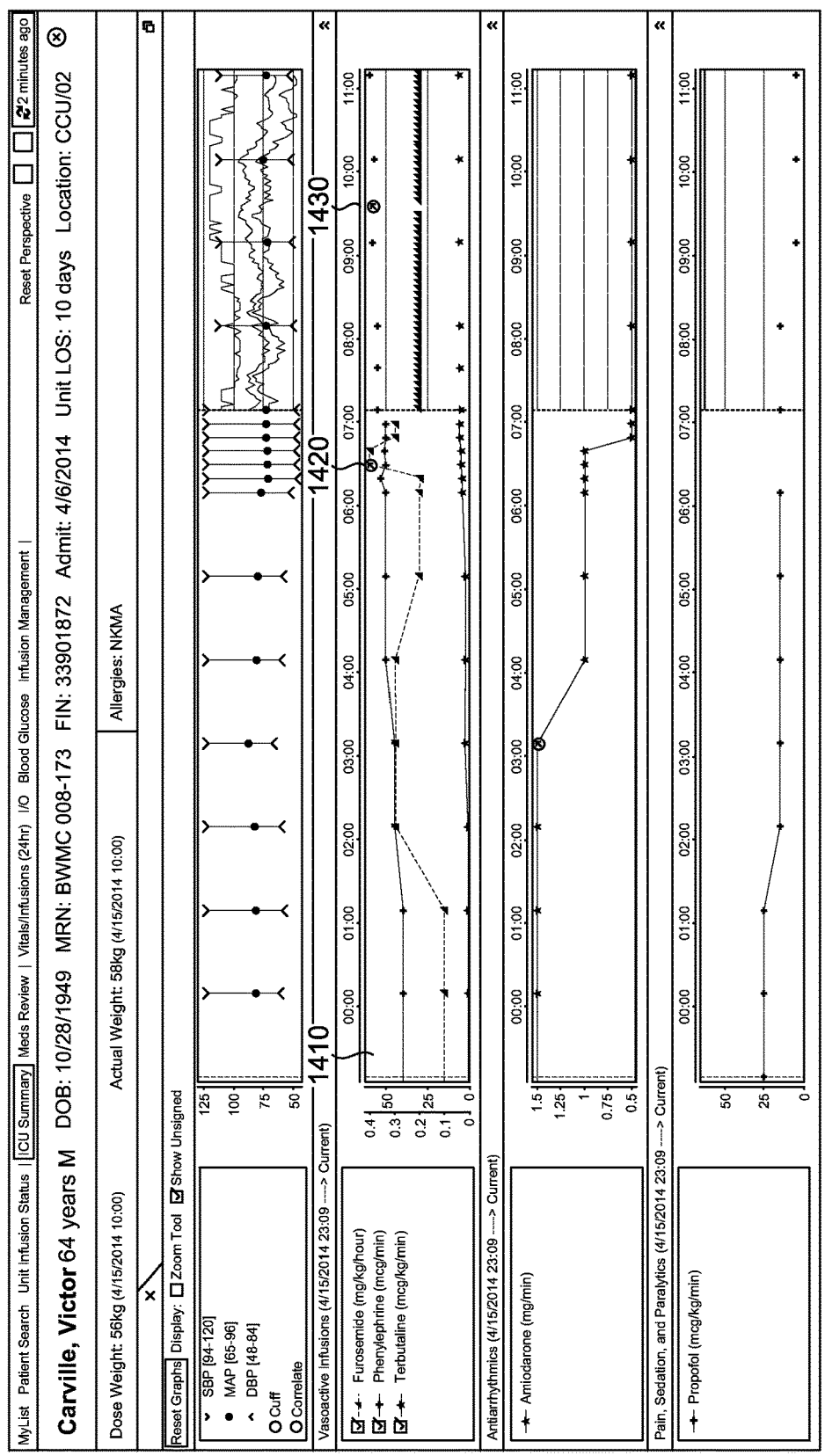

Referring to FIG. 14, an illustrative graphical user interface 1400 showing a plurality of infusions is shown, in accordance with embodiments of the present invention. Once an infusion has been signed, a graphical representation of the infusions 1410 over time is shown. Bolus indicators 1420 are depicted to show when the bolus was given. As indicated, when the bolus is administered, the level of the medication is shown much higher than before the bolus was administered.

Figure 15:
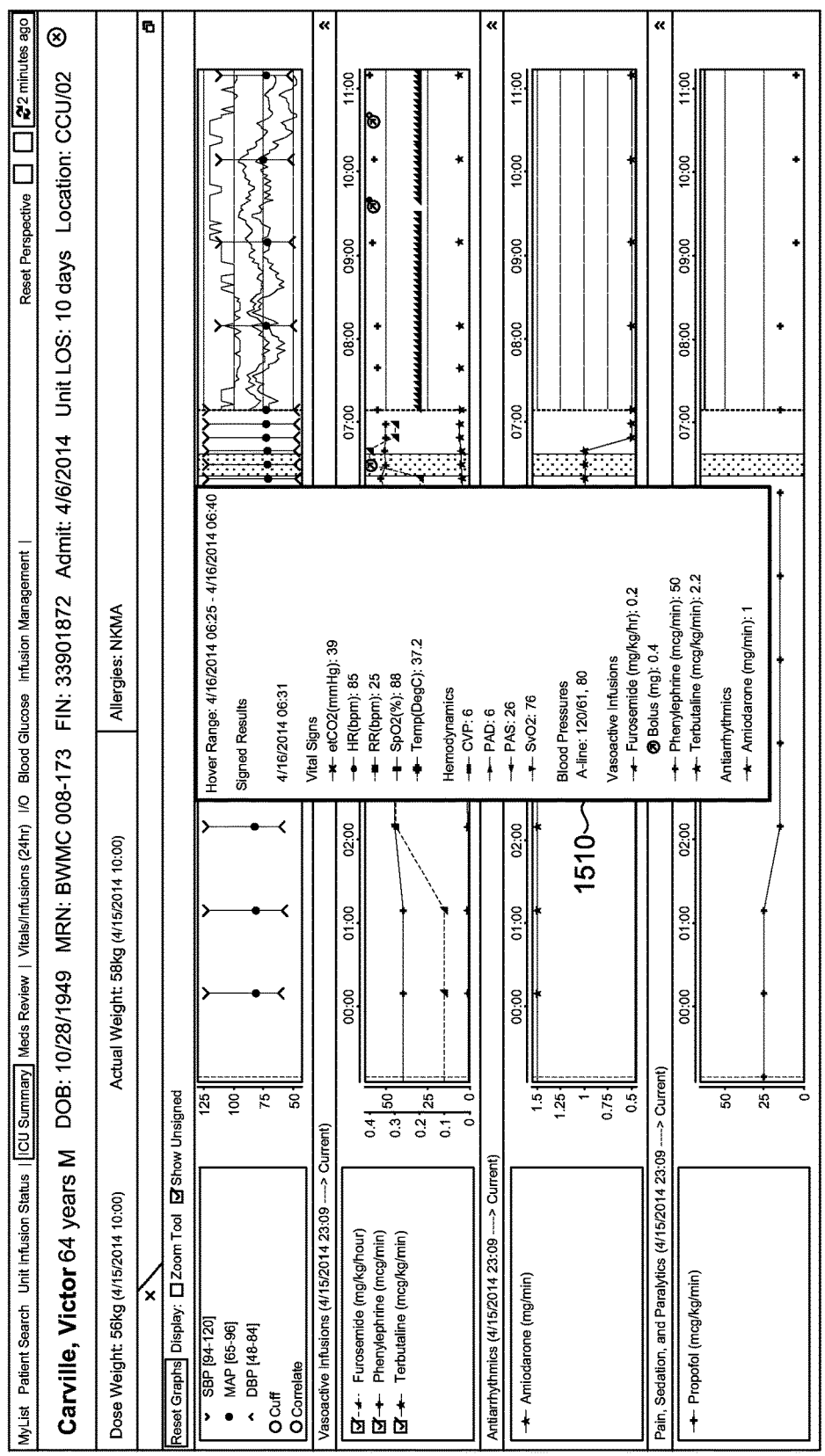

Referring next to FIG. 15, an illustrative graphical user interface 1500 is shown of infusion data for a patient. Upon an interaction with a point in time on the graph, a dialogue box 1510 opens providing signed results for the patient. The signed results may include vital signs, hemodynamics, blood pressures, vasoactive infusions, and other medications.

Referring to FIGS. 16-19, illustrative graphical user interfaces 1600, 1700, 1800, and 1900 are shown for an infusion pump that does not automatically send bolus information, in accordance with embodiments of the present invention. As shown for the medication 1610, there is no bolus row. However, interacting with the medication 1610 causes dialogue box 1710 to open. A clinician can then select the document bolus icon 1720 to add a bolus row 1810. The clinician can then document the strength 1910 of the bolus.

Figure 21:
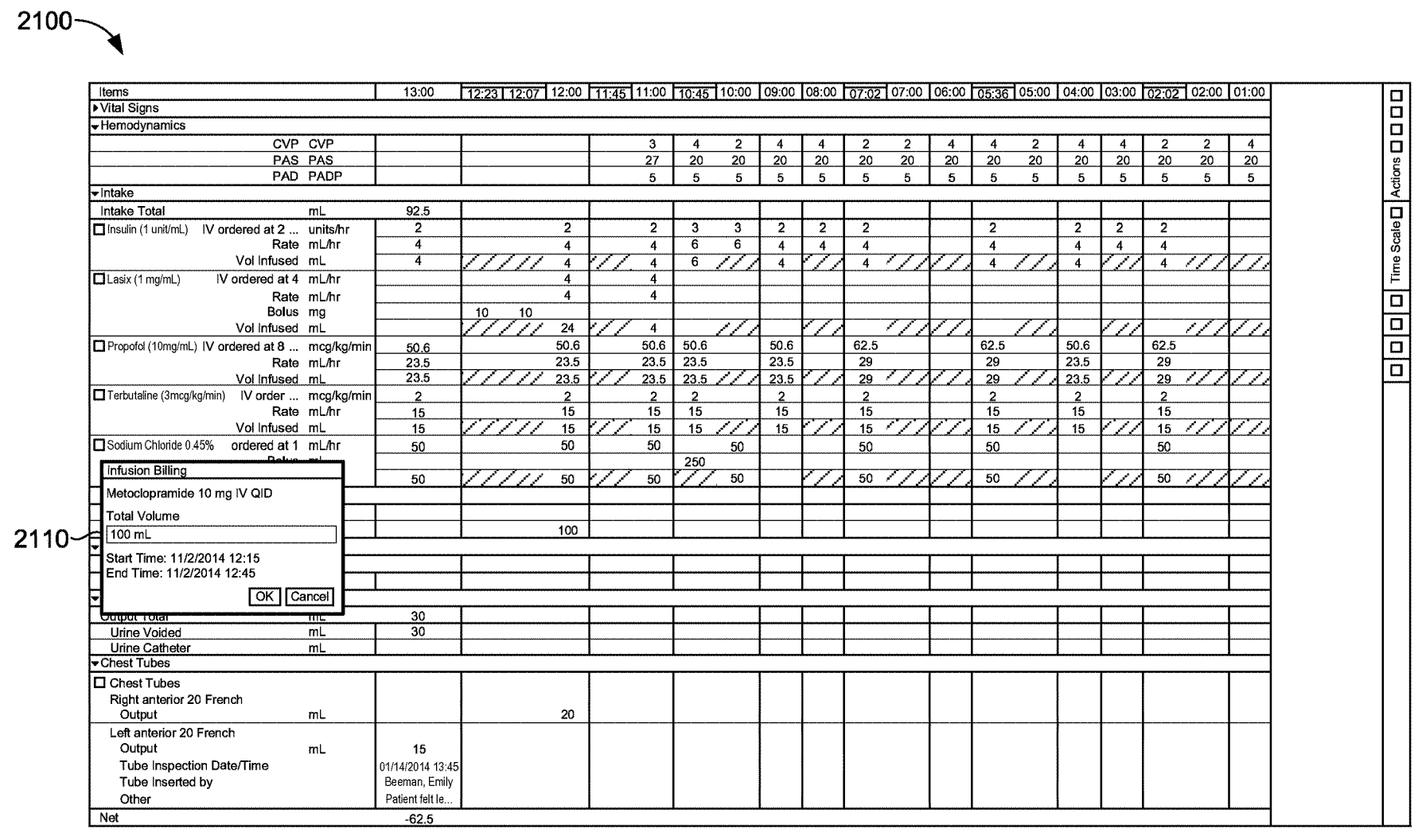

FIG. 21 are illustrative graphical user interfaces 2000, 2100 for infusion billing in accordance with embodiments of the present invention. Based on an encounter type, infusion billing may be initiated by interacting with a particular infusion causing a dialogue box 2010 to open. Upon selecting a billing link within the dialogue box 2010, another dialogue box 2110 is opened allowing adjustments to be made. The billing link is specific to a medication and the additional dialogue box 2110 provides order information, total volume, start and end time (as communicated by the pump), each of which may be adjusted, if necessary. For example, times may need to be adjusted if the patient has been moved. This allows for two separate charges, based on department, even if the same bag is used. Upon selecting OK, the information is provided to a billing service.

Figure 22:
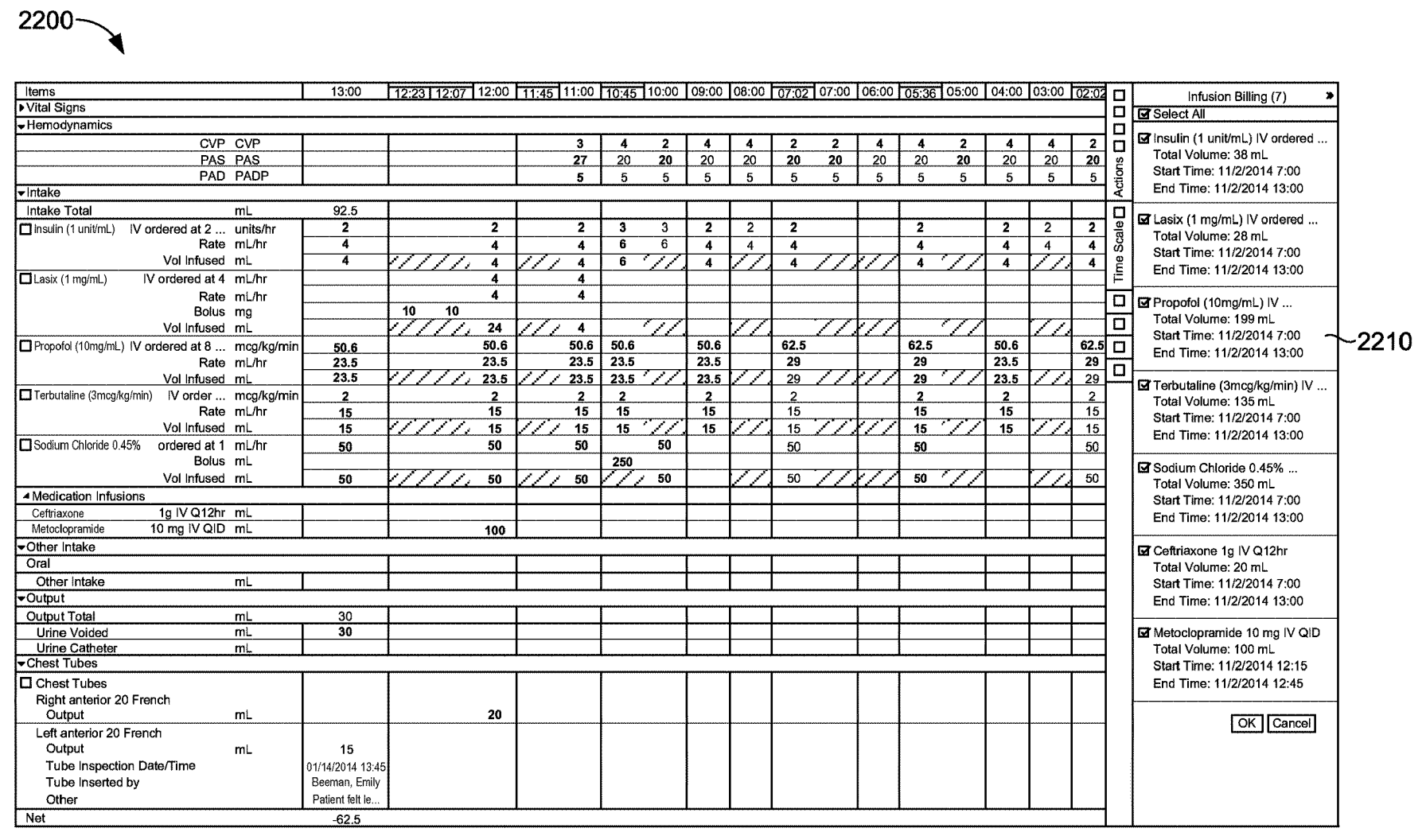

Turning to FIG. 22, graphical user interface 2200 depicting all infusions 2210 that need to be signed for a patient is shown, in accordance with embodiments of the present invention. Once the infusions are signed, they are provided to the billing service. As mentioned above, the total volume is editable and the start and end times may be hyperlinks. For example, if a patient is transferred, a clinician in the transferring unit may edit the end time based on the time the patient was transferred. Similarly, a clinician in the receiving unit may edit the start and end times based on the time the patient was in the receiving unit. This allows both the transferring and receiving unit to charge for the infusion based on the time the patient was actually receiving the infusion in the respective unit. Once a bolus is signed, the corresponding infusion is also signed.

Turning to FIG. 23, an illustrative graphical user interface 2300 of device association is shown, in accordance with embodiments of the present invention. Any associated devices may appear in an associated devices area 2310 and a device search area 2320 may enable a clinician to search for a particular device. This may allow a clinician to locate a missing device or identify available devices (and their locations).

Figure 24:
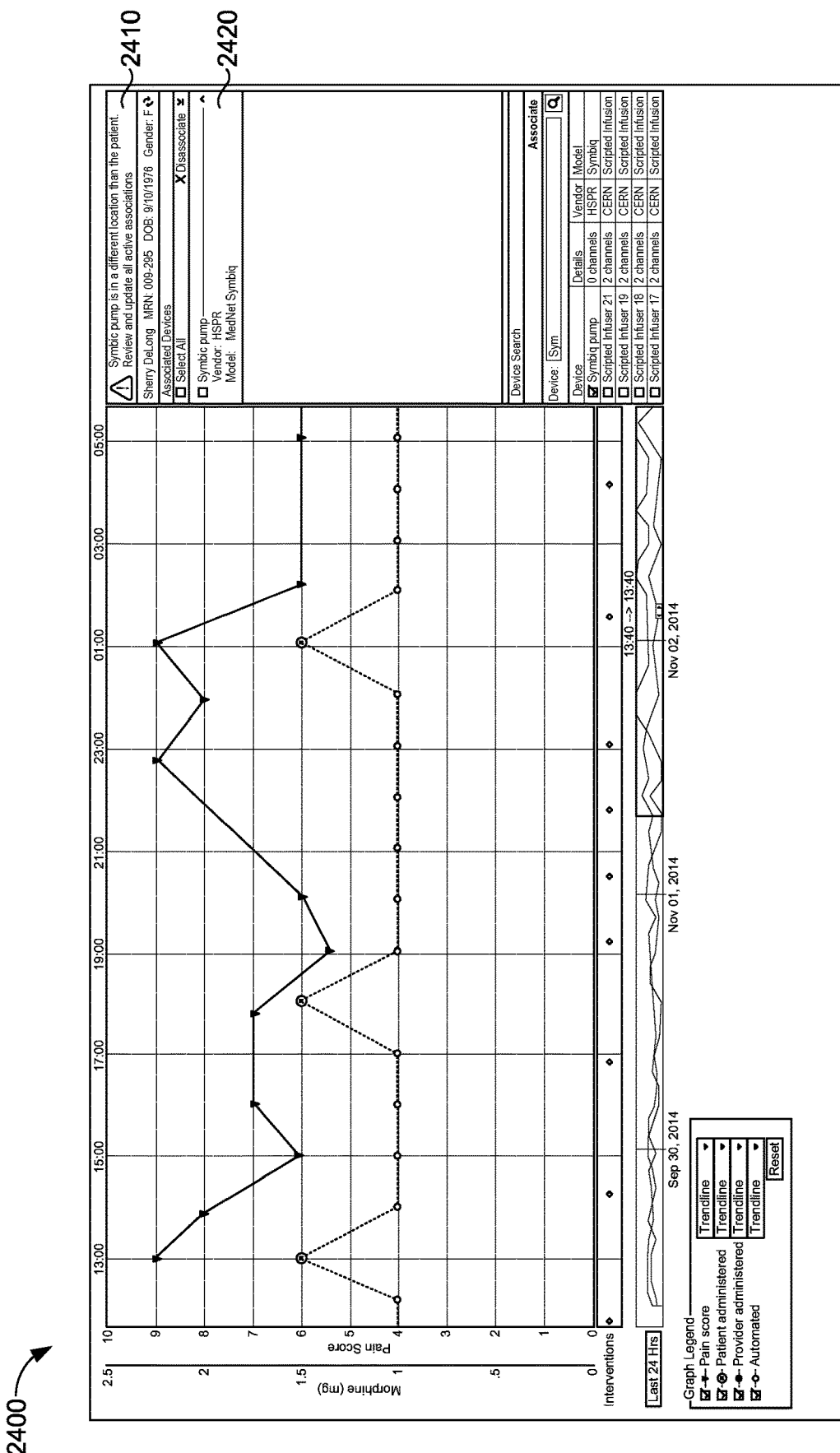
Figure 25:
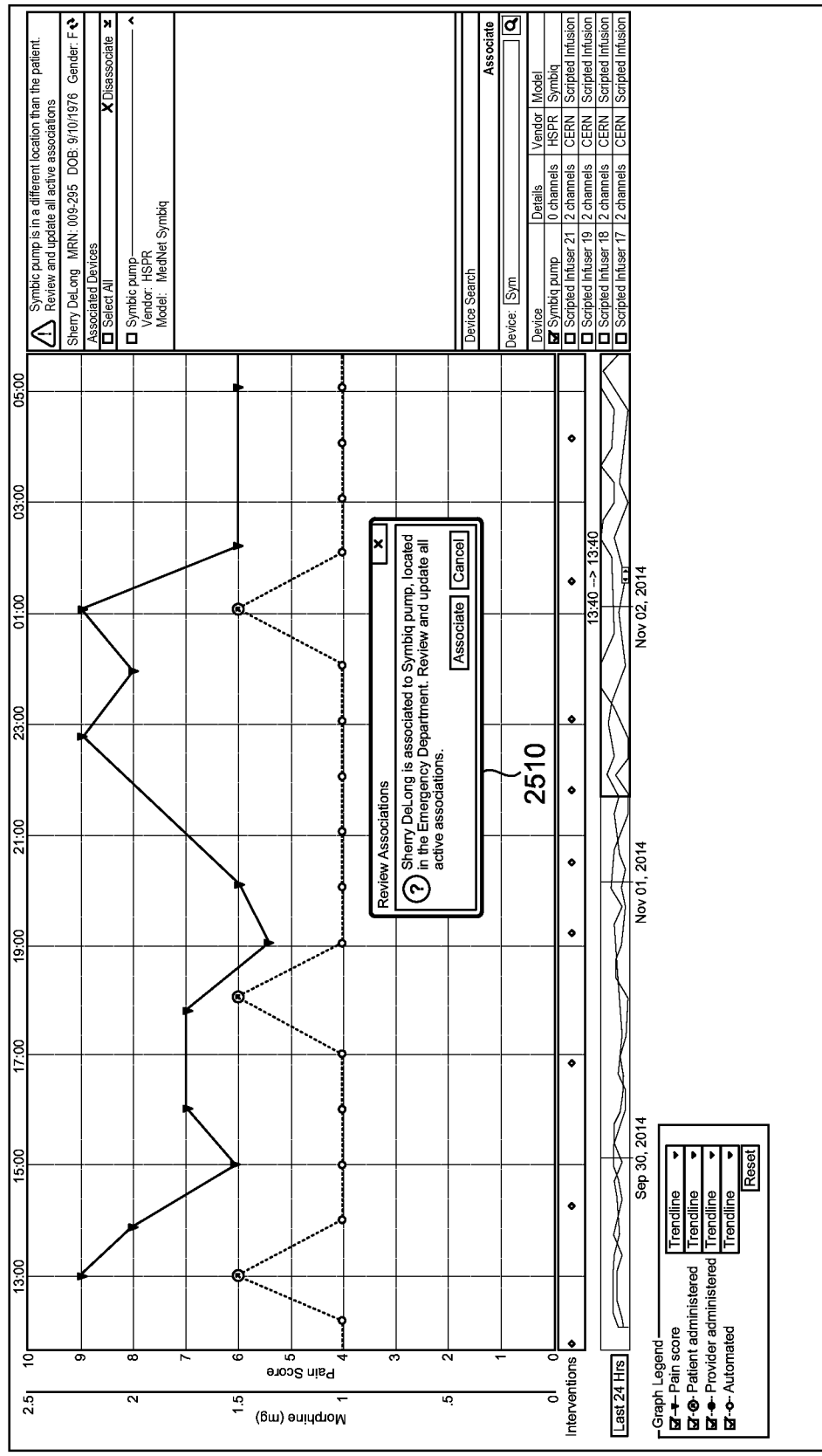

FIGS. 24 and 25 are illustrative graphical user interfaces 2400, 2500 of device association, in accordance with embodiments of the present invention. As illustrated, alerts 2410, 2510 are provided when the device is in a different location than the patient. The clinician may then review all associated devices 2420 to identify the source of the alert and disassociate the device accordingly.

Figure 27:
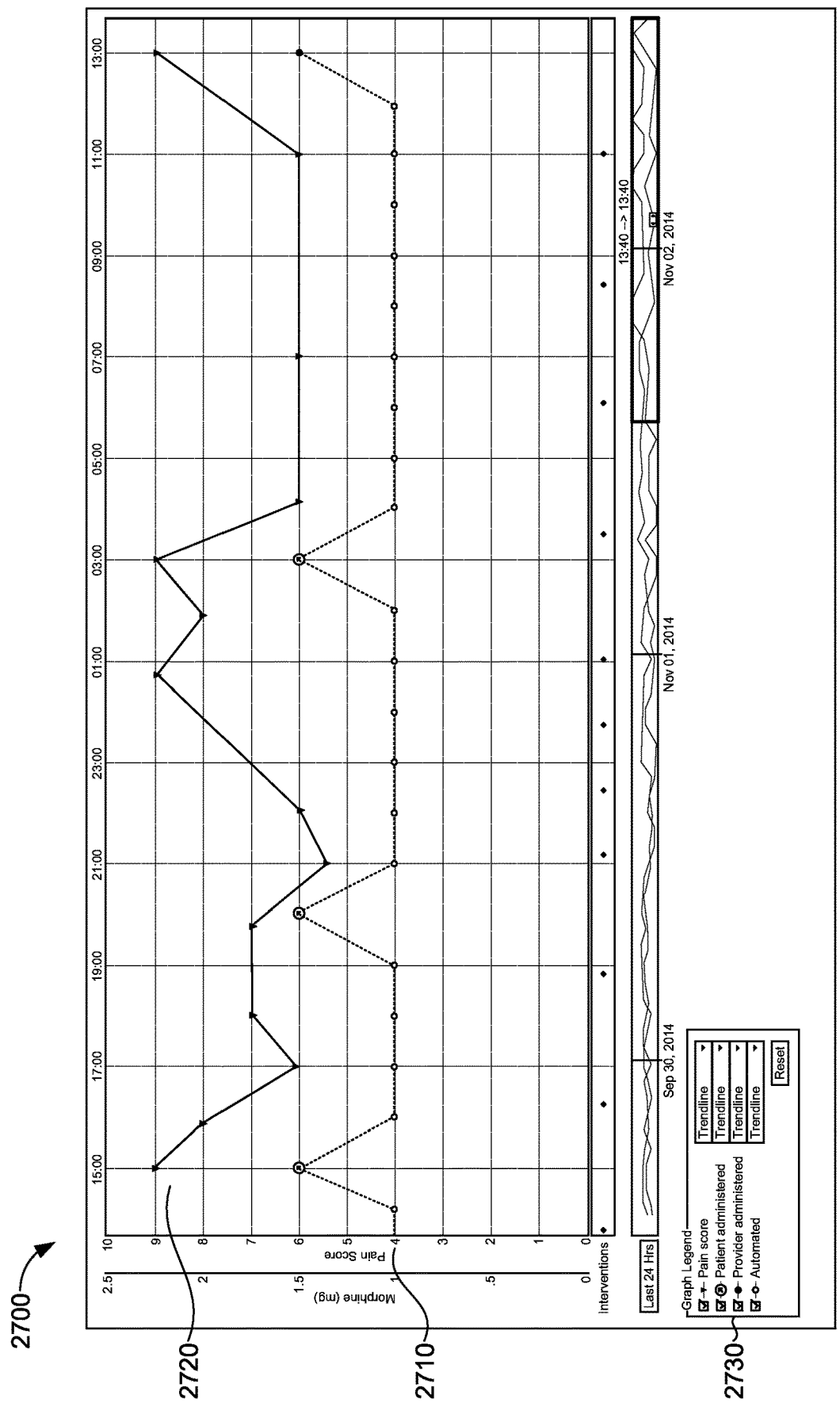
Figure 28:
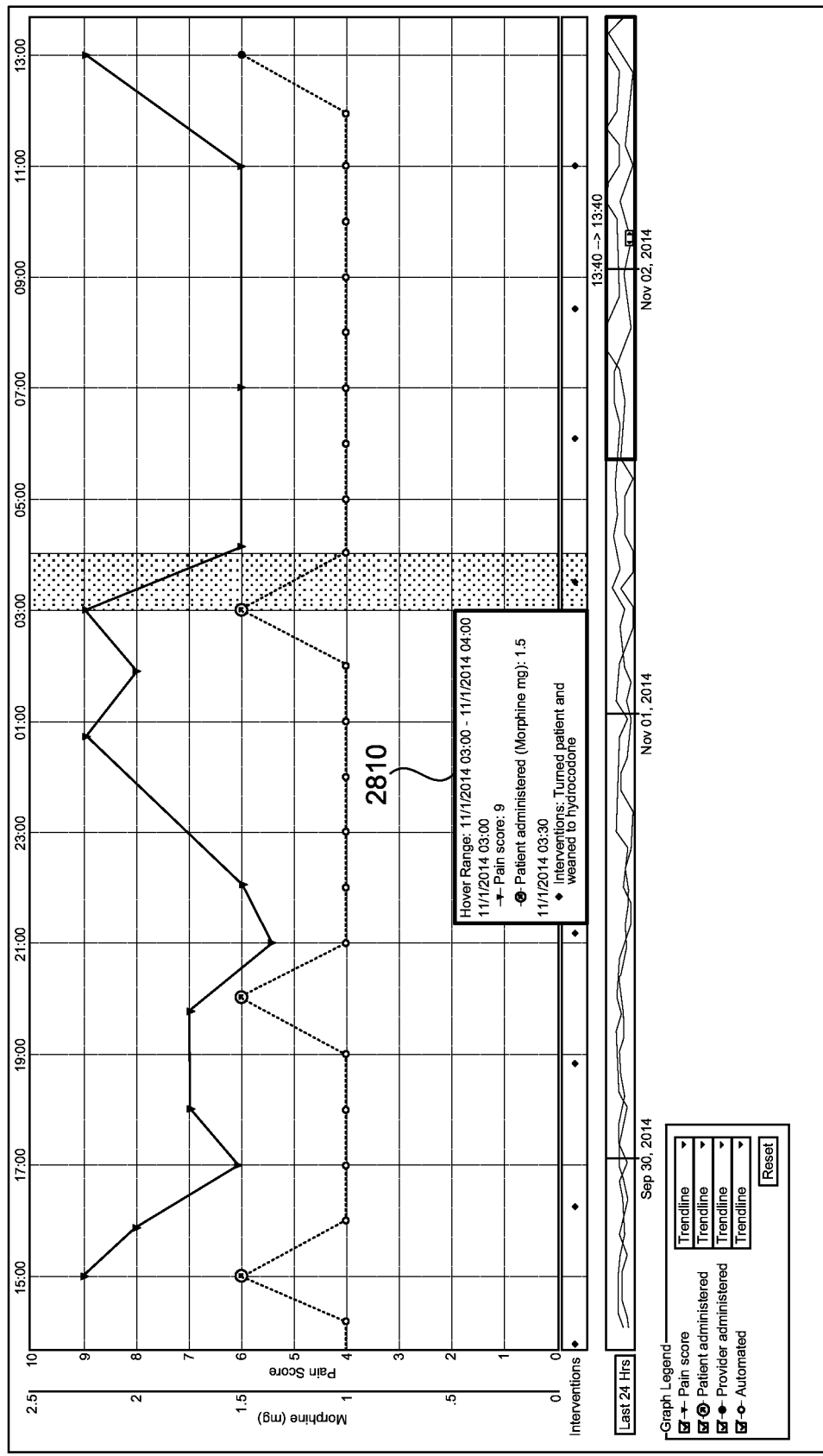

Turning to FIG. 26-28, graphical user interfaces 2600, 2700, and 2800 corresponding to patient controlled analgesia and epidural information, in accordance with embodiments of the present invention. The information 2610 includes clinician dose, patient dose, number of attempted doses, and number of doses delivered. A graphical view 2700 showing the correlation between the pain score or sedation score 2710 and the amount of medication 2720 is shown as well as a legend 2730 that helps a clinician identify how the medication was administered (patient administered, provider administered, or automated). By interacting with a portion of the graph, a dialogue box 2810 opens and provides the pain score or sedation score for that time period, the amount of medication administered (including who administered it), interventions, and the like.

Turning now to FIG. 29, a flow diagram is provided that illustrates a method 2900 for bolus display and documentation in accordance with embodiments of the present invention. At block 2910, information is received from an infusion device. The information may include one or more of start time, stop time, duration, rate, dose, or volume of an infusion. The information may be automatically provided by the infusion device. An indication is received, at block 2912, that a bolus is being administered to a patient in association with the infusion. The indication may be automatically provided by the infusion device. In other embodiments, the indication that a bolus is being administered to the patient in association with the infusion is received from a clinician. At block 2914, a graphical indication that the bolus is running in association with the infusion is provided, via a user interface. The graphical indication causes a volume remaining and the rate of the infusion to be temporarily masked. In embodiments, while the bolus is being administered to the patient, an ordered rate of infusion is provided instead of a current rate of infusion. Upon the bolus completing, at block 2916, the volume remaining and the rate of the infusion are provided, via the user interface.

In some embodiments, the appearance of the graphical indication is altered if a bag for the infusion needs to be replaced once the bolus is complete. In some embodiments, the graphical indication is provided to a pharmacy view interface. The pharmacy view interface comprises a plurality of infusions for a plurality of patients and may be provided, for example, by infusion application 232 of FIG. 2, as described above. The graphical indication enables the pharmacists to recognize when a bolus is being administered. This prevents the pharmacists from mistakenly and prematurely preparing new infusion bags, which can be extremely costly.

In some embodiments, upon receiving an interaction with a total volume of the infusion via the user interface, a dialogue box identifying an amount of the bolus and an amount of the infusion is provided. A duration of the bolus may be calculated and provided via the user interface. Similarly, a strength of the bolus may be provided via the user interface.

In some embodiments, a bolus row is added to the user interface when the bolus completes. In some embodiments, upon receiving an interaction with the infusion via the user interface, a dialogue box is opened. The dialogue box contains an icon that allows the clinician to add a bolus row to the user interface and document a strength of the bolus. The volume infused by infusion may be provided separately from the volume infused by bolus. An altered appearance may be provided for infusions that have not been signed by a clinician. The infusion may be automatically signed after a corresponding bolus has been signed.

With reference now to FIG. 30 a flow diagram is provided that illustrates a method 3000 for infusion billing in accordance with embodiments of the present invention. At block 3010, a graphical indication is provided, via a user interface, that an infusion is being administered to a patient. The graphical indication may include a volume of the infusion. An interaction with the graphical indication is received, at block 3012, via the user interface.

Upon receiving the interaction, a billing link is provided for the infusion, at block 3014, via the user interface. The billing link may be specific to a medication. A selection of the billing link is received via the user interface, at block 3016. Upon receiving a selection of the billing link, encounter specific infusion information is provided, at block 3018, via the user interface. The encounter specific infusion information may include order information, total volume administered, start and end time provided via an infusion device. At block 3020, the encounter specific infusion information is provided to a billing service. In some embodiments, an indication the infusion has been signed by a clinician is received prior to providing the encounter specific infusion information to the billing service.

In some embodiments, adjustments to the infusion information are received, via the user interface. The adjustments may include time adjustments when a patient has been moved. For example, the patient may have been moved to another unit of a healthcare facility. In this case, the billing service separates the charges in accordance with a portion of the infusion provided to the patient in each unit of the healthcare facility as indicated by the time adjustments. In some embodiments, the charges are separate even when the same bag is used in more than one unit of the healthcare facility.

Turning now to FIG. 31, a flow diagram is provided that illustrates a method 3100 for disassociating devices in accordance with embodiments of the present invention. At block 3110, an indication that a device is associated to a patient is received. An alert is provided to a clinician, at block 3112. Indicating that the device is in a different location than the patient or that a similar device is already associated to the patient. An identification of the different location may be provided. In some embodiments, the clinician may be prompted to disassociate the device from the patient.

In some embodiments, characteristics of the device are received. Based on the characteristics of the device or information received from the device, it is determined whether the device is primary or secondary. In some embodiments, the device is modified from secondary to primary.

Vendor identification and a model of the device may be provided via a user interface. A graphical trend of when the device and any other devices associated to the patient may also be provided. The graphical trend identifies the type of the device and the type of any other devices, including any medications associated with the device or other devices. The user interface may enable the clinician to search for a particular device.

With reference now to FIG. 32 a flow diagram is provided that illustrates a method 3200 for providing pain score or sedation score management for patient controlled analgesia and epidurals in accordance with embodiments of the present invention. At block 3210, information is received from an infusion device. The information may include duration, rate, dose, or volume of an infusion. The information may include whether the infusion was patient administered, provider administered, or automated. The information may include an indication of a number of doses attempted. The information may include an indication of a number of doses delivered. Any or all of the information may be provided via a user interface.

At block 3212, a pain score or sedation score is received for a patient. The pain score or sedation score is correlated with the infusion. In other words, the pain score or sedation score is associated with the same point in time as the infusion so a clinician can identify how the patient is responding to the medications. A graphical representation is provided via a user interface, at block 3214, indicating the correlation between the information and the pain score or sedation score. A type of medication associated with the infusion may similarly be provided via the user interface.

In some embodiments, vital signs associated with each dose delivered via the infusion are received. The vital signs may be automatically taken each time a dose is attempted or delivered via the infusion. A graphical representation may be provided, via the user interface, indicating a correlation between the information and the vital signs.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. One or more non-transitory computer storage media storing computer-useable instructions that, when used by one or more computing devices, cause the one or more computing devices to perform operations comprising:
  receiving information from an infusion device associated with a patient in a healthcare facility, the information including start time, stop time, duration, rate, dose, and volume of an infusion;
  providing to a clinician a user interface of the patient's electronic medical records on a computing device separate from the infusion device;
  displaying, on the user interface of the patient's electronic medical records, the received information from the infusion device;
  receiving an indication, via the infusion device or based on a clinician interaction with a computing device user interface, that a bolus is being administered to a patient in association with the infusion;
  upon the bolus starting, providing, on the computing device user interface, a first graphical indication causing a time remaining and rate of infusion to be temporarily masked for the duration of the bolus;
  during administration of bolus, providing, on the computing device user interface, a second graphical indication to indicate if a bag for the infusion needs to be replaced, the second graphical indication being provided simultaneously with the first graphical indication wherein, the second graphical indication causes a volume remaining to be masked;
  upon the bolus completing, providing, on the computing device user interface, the volume of the bolus remaining and the rate of the infusion; and
  communicating and storing, indications from the computing device user interface and information from the infusion device, to a the patient's electronic medical record.

2. The media of claim 1, further comprising, while the bolus is being administered to the patient, providing an ordered rate of infusion instead of a current rate of infusion.

3. The media of claim 1, further comprising altering the appearance of the graphical indication if a bag for the infusion needs to be replaced once the bolus is complete.

4. The media of claim 1 further comprising providing the graphical indication to a pharmacy view interface, the pharmacy view interface comprising a plurality of infusions for a plurality of patients.

5. The media of claim 1, further comprising adding a bolus row to the user interface when the bolus completes.

6. The media of claim 1, further comprising receiving an interaction with a total volume of the infusion.

7. The media of claim 6, further comprising providing, via the user interface, a dialogue box identifying an amount of the bolus and an amount of the infusion upon receiving the interaction.

8. The media of claim 7, further comprising, calculating and providing a duration of the bolus.

9. The media of claim 7, further comprising, providing strength of the bolus.

10. The media of claim 1, further comprising providing, via the user interface, a volume infused by infusion separate from a volume infused by bolus.

11. The media of claim 10, further comprising, providing, via the user interface, an altered appearance for infusions that have not been signed by a clinician.

12. The media of claim 1, further comprising, automatically signing an infusion after a corresponding bolus has been signed.

13. The media of claim 1, wherein the indication that the bolus is being administered to the patient in association with the infusion is received from the infusion device.

14. The media of claim 1, wherein the indication that the bolus is being administered to the patient in association with the infusion is received from a clinician.

15. The media of claim 14, further comprising receiving an interaction with the infusion.

16. The media of claim 15, further comprising opening a dialogue box containing an icon that allows the clinician to add a bolus row to the user interface and document a strength of the bolus or a fluid bolus for a specific medication.

17. A computer-implemented method in a clinical computing environment comprising:

receiving information from an infusion device associated with a patient in a healthcare facility, via a first computing process, the information including start time, stop time, duration, rate, dose, and volume of an infusion;

providing, via a second computing process, to a clinician a user interface of the patient's electronic medical records on a computing device separate from the infusion device;

displaying, via a third computing process, on the user interface of the patient's electronic medical records, the received information from the infusion device;

receiving, via a fourth computing process, an indication, via the infusion device or based on a clinician interaction with the computing device user interface, that a bolus is being administered to a patient in association with the infusion, the indication being received from the infusion device;

providing, via a fifth computing process, a first graphical indication on the computing device user interface that the bolus is running in association with the infusion, the graphical indication causing a time remaining and the rate of the infusion to be temporarily masked for the duration of the bolus;

during administration of bolus, providing, via a sixth computing process, on the computing device user interface a second graphical indication to indicate if a bag for the infusion needs to be replaced, the second graphical indication being provided simultaneously with the first graphical indication wherein, the second graphical indication causes a volume remaining to be masked;

upon the bolus completing, providing, via a seventh computing process, on the computing device user interface the volume of the bolus remaining and the rate of the infusion; and communicating and storing, via an eighth computing process, indications from the computing device user interface and information from the infusion device, to the patient's electronic medical record;

wherein each computing process is performed by one or more computing devices.

18. The media of claim 17 further comprising providing, via a ninth computing process, the graphical indication to a pharmacy view interface, the pharmacy view interface comprising a plurality of infusions for a plurality of patients.

19. A system comprising:

one or more processors; and one or more computer storage media storing instructions that, when used by the one or more processors, cause the one or more processors to:

receive information from an infusion device associated with a patient in a healthcare facility, the information including start time, stop time, duration, rate, dose, and volume of an infusion;

provide to a clinician a user interface of the patient's electronic medical records on a computing device separate from the infusion device;

display, on the user interface of the patient's electronic medical records, the received information from the infusion device;

receive an indication, via the infusion device or based on a clinician interaction with the computing device user interface, that a bolus is being administered to a patient in association with the infusion;

provide, on the computing device user interface, a first graphical indication that the bolus is running in association with the infusion, the indication causing a time remaining and the rate of the infusion to be temporarily masked for the duration of the bolus;

provide during administration of bolus, on the computing device user interface, a second graphical indication to indicate if a bag for the infusion needs to be replaced, the second graphical indication being provided simultaneously with the first graphical indication wherein, the second graphical indication causes a volume remaining to be masked;

upon the bolus completing, provide, on the computing device user interface, the volume of the bolus remaining and the rate of the infusion; and communicate, indications from the computing device user interface and information from the infusion device, to the patient's electronic medical record.

* * * * *

UNITED STATES PATENT AND TRADEMARK OFFICE
CERTIFICATE OF CORRECTION

PATENT NO. : 10,929,480 B2  
APPLICATION NO. : 14/587493  
DATED : February 23, 2021  
INVENTOR(S) : Lisa Kelly et al.

Page 1 of 1

It is certified that error appears in the above-identified patent and that said Letters Patent is hereby corrected as shown below:

In the Specification

Column 07, Line 44: Please remove "Electronic" and replace with --Electronics--.

Column 17, Line 13: After "based on" please add --the--.

Column 17, Line 46: Please remove "FIG." and replace with --FIGS.--.

In the Claims

Column 20, Line 48: Please remove "to a the" and replace with --to the--.

Column 22, Line 15: Please remove "media" and replace with --method--.

Signed and Sealed this  
Sixth Day of April, 2021

Drew Hirshfeld  
*Performing the Functions and Duties of the  
Under Secretary of Commerce for Intellectual Property and  
Director of the United States Patent and Trademark Office*